(12) United States Patent
De Pizzol et al.

(10) Patent No.: US 10,508,090 B2
(45) Date of Patent: Dec. 17, 2019

(54) SULFONAMIDES AS GPR40- AND GPR120-AGONISTS

(71) Applicant: DOMPÉ FARMACEUTICI S.P.A., Milan (IT)

(72) Inventors: Maria De Pizzol, Milan (IT); Anna Sirico, Somma Vesuviana (IT); Mara Zippoli, Genoa (IT); Gianluca Bianchini, L'Aquila (IT); Andrea Beccari, L'Aquila (IT); Andrea Aramini, L'Aquila (IT); Chiara Rossana Maria Liberati, Milan (IT)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 0 days.

(21) Appl. No.: 16/324,243

(22) PCT Filed: Aug. 7, 2017

(86) PCT No.: PCT/EP2017/069958
§ 371 (c)(1),
(2) Date: Feb. 8, 2019

(87) PCT Pub. No.: WO2018/029150
PCT Pub. Date: Feb. 15, 2018

(65) Prior Publication Data
US 2019/0169142 A1    Jun. 6, 2019

(30) Foreign Application Priority Data

Aug. 9, 2016  (EP) .................................. 16183294

(51) Int. Cl.
| | | |
|---|---|---|
| *C07C 311/16* | (2006.01) | |
| *C07C 311/20* | (2006.01) | |
| *C07C 311/21* | (2006.01) | |
| *C07C 311/51* | (2006.01) | |
| *C07D 231/42* | (2006.01) | |
| *C07D 235/30* | (2006.01) | |
| *C07D 249/04* | (2006.01) | |
| *C07D 249/08* | (2006.01) | |
| *C07D 249/14* | (2006.01) | |
| *C07D 257/06* | (2006.01) | |
| *C07D 261/16* | (2006.01) | |
| *C07D 263/30* | (2006.01) | |
| *C07D 275/03* | (2006.01) | |
| *C07D 277/52* | (2006.01) | |
| *C07D 285/04* | (2006.01) | |
| *C07D 285/135* | (2006.01) | |

(Continued)

(52) U.S. Cl.
CPC ........ *C07D 285/135* (2013.01); *C07C 311/16* (2013.01); *C07C 311/20* (2013.01); *C07C 311/21* (2013.01); *C07C 311/51* (2013.01); *C07D 231/42* (2013.01); *C07D 235/30* (2013.01); *C07D 249/04* (2013.01); *C07D 249/08* (2013.01); *C07D 249/14* (2013.01); *C07D 257/06* (2013.01); *C07D 261/16* (2013.01); *C07D 263/28* (2013.01); *C07D 263/30* (2013.01); *C07D 263/50* (2013.01); *C07D 275/03* (2013.01); *C07D 277/52* (2013.01); *C07D 285/04* (2013.01); *C07D 285/08* (2013.01); *A61P 3/04* (2018.01); *A61P 3/06* (2018.01); *A61P 3/10* (2018.01)

(58) Field of Classification Search
CPC ... C07C 311/16; C07C 311/20; C07C 311/21; C07C 311/51; C07D 231/42; C07D 235/30; C07D 249/04; C07D 249/08; C07D 249/14; C07D 257/06; C07D 261/16; C07D 263/30; C07D 275/03; C07D 277/52; C07D 285/04; C07D 285/135

See application file for complete search history.

(56) References Cited

U.S. PATENT DOCUMENTS

2011/0184031 A1   7/2011  Tsujimoto et al.
2015/0274672 A1  10/2015  Chelliah et al.

FOREIGN PATENT DOCUMENTS

WO   WO2011042465   4/2011
WO   WO2014073904   5/2014
(Continued)

OTHER PUBLICATIONS

Adrian, Javier, et al., "Generation of broad specificity antibodies for sulfonamide antibiotics and development of an enzyme-linked immunosorbent assay (ELISA) for the analysis of milk samples" J. Agric. Food Chem., 2009, 57, pp. 385-394.

(Continued)

*Primary Examiner* — Laura L Stockton
(74) *Attorney, Agent, or Firm* — Hueschen and Sage

(57) ABSTRACT

The invention relates to compounds acting as agonists of G-protein coupled receptor 120 (GPR120) and/or 40 (GPR40), and having formula (I):

(I)

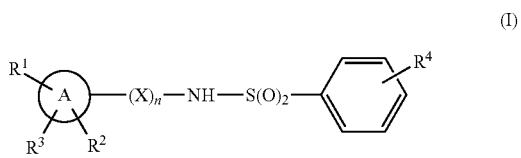

Said compounds are useful in the treatment of diseases or disorders modulated by GPR120 and/or GPR40 such as diabetes (particularly type 2 diabetes), impaired oral glucose tolerance, insulin resistance, obesity, obesity related disorders, metabolic syndrome, dyslipidemia, elevated LDL, elevated triglycerides, obesity induced inflammation, osteoporosis and obesity related cardiovascular disorders.

15 Claims, No Drawings

(51) Int. Cl.
  C07D 263/50  (2006.01)
  C07D 263/28  (2006.01)
  C07D 285/08  (2006.01)
  A61P 3/04  (2006.01)
  A61P 3/06  (2006.01)
  A61P 3/10  (2006.01)

(56) References Cited

FOREIGN PATENT DOCUMENTS

WO  WO2014209034  12/2014
WO  WO2016057731  4/2016

OTHER PUBLICATIONS

Briscoe, Celia, P., et al., "The orphan G protein-coupled receptor GPR40 is activated by medium and long chain fatty acids", The Journal of Biological Chemistry, vol. 278, No. 13, Mar. 2003, pp. 11303-11311.

Cornish, Jillian, et al., "Modulation of osteoclastogenesis by fatty acids", Endocrinology, 149(11), 2008, pp. 5688-5695.

Drucker, Daniel, J., "The biology of incretin hormones", Cell Metabolism, Mar. 3, 2006, pp. 153-165.

Edfalk, Sara, et al., "Gpr40 is expressed in enteroendocrine cells and mediates free fatty acid stimulation of incretin secretion", Diabetes, vol. 57, Sep. 2008, pp. 2280-2287.

Finn, Paul, W., et al., "Novel sulfonamide derivatives as inhibitors of histone deacetylase", Helvetica Chimica Acta, vol. 88, 2005, pp. 1630-1656.

Gotoh, Chizu, et al., "The regulation of adipogenesis through GPR120", Biochemical and Biophysical Research Communications, 354, 2007, pp. 591-597.

Hirasawa, Akira, et al., "Free fatty acids regulate gut incretin glucagon-like peptide-1 secretion through GPR120", Nature Medicine, vol. 11, No. 1, Jan. 2005, pp. 90-94.

Hudson, B.D., et al., Experimental challenges to targeting poorly characterized GPCRs: uncovering the terapeutic potential for free fatty acid receptors, Advances in Pharmacology, vol. 62, pp. 175-218, 2011.

Ichimura, Atsuhiko, et al., "Dysfunciton of lipid sensor GPR120 leads to obesity in both mouse and human", Nature, vol. 000, 2012, pp. 1-8.

International Search Report for PCT/EP2017/069958 dated Oct. 19, 2017.

Liou, Alice, P., et al., "The G-protein-coupled receptor GPR40 directly mediates long-chain fatty acid-induced secretion of cholecystokinin", Gastroenterology, 2011, pp. 903-912.

Mannucci, E., et al., "Glucagon-like peptide (GLP)-1 and leptin concentrations in obese patients with type 2 diabetes mellitus", Diabetic Medicine, 17, 2000, pp. 713-719.

Oh, Da Young, et al., "A GPR120-selective agonist improves insulin resistance and chronic inflammation in obese mice", Nature Medicine, vol. 20, No. 8, Aug. 2014, pp. 942-949.

Oh, Da Young, et al., "GPR120 is an omega-3 fatty acid receptor mediating potent anti-inflammatory and insulin-sensitizing effects", Cell, 142, Sep. 2010, pp. 687-698.

Tanaka, Toshiki, et al., "Free fatty acids induce cholecystokinin secretion through GPR120", Naunyn-Schmiedeberg's Arch Pharmacol, 377, 2008, pp. 523-527.

Taneera, Jalal, et al., "A systems genetics approach identifies genes and pathways for type 2 diabetes in human islets", Cell Metabolism, Jul. 16, 2012, pp. 122-134.

SULFONAMIDES AS GPR40- AND GPR120-AGONISTS

BRIEF DESCRIPTION OF THE INVENTION

The present invention relates to compounds that acts as G-protein coupled receptor 120 (GPR120) and/or 40 (GPR40) agonists, pharmaceutical compositions containing them and their use in the treatment of diseases or disorders modulated by said GPRs such as diabetes (particularly type 2 diabetes), impaired oral glucose tolerance, insulin resistance, obesity, obesity related disorders, metabolic syndrome, dyslipidemia, elevated LDL, elevated triglycerides, obesity induced inflammation, osteoporosis and obesity related cardiovascular disorders.

BACKGROUND OF THE INVENTION

G protein-coupled receptors (GPCRs) superfamily is comprised of receptors involved in the detection of a wide range of chemicals, including nutrients, hormones and neurotransmitters. GPR40 and GPR120, also known as free fatty acid receptors 1 and 4 (FFA1-4), are both activated by medium- and long-chain saturated and unsaturated fatty acids derived from dietary triglycerides [Hudson B. D. et al., Adv Pharmacol (2011), 62: p. 175-218]. In humans and rodents GPR40 was initially shown to be expressed in different regions of brain and in pancreatic beta cell [Briscoe C. P. et al., J Biol Chem (2003), 278(13): p. 11303-11] where GPR40 activation leads to increased intracellular calcium levels and consequent insulin secretion. GPR40 is also expressed by gut enteroendocrine cells [Edfalk, S. et al., Diabetes (2008), 57(9): p. 2280-7; Liou A. P. et al., Gastroenterology (2011), 140(3): p. 903-12] where the receptor is activated by fatty acids, generating the release of incretin hormones such as glucagon-like peptide-1 (GLP-1). GPR120 is highly expressed in the intestine (enteroendocrine L cell of the colon and cell lines such as STC-1), but also in the lung, thymus, spleen, and pancreas [Hirasawa A. et al., Nat Med (2005), 11(1): p. 90-4; Taneera J. et al., Cell Metab (2012), 16(1): p. 122-34; Tanaka T. et al., Naunyn Schmiedebergs Arch Pharmacol (2008), 377(4-6): p. 523-7].

As for GPR40, activation of GPR120 on enteroendocrine cells contributes to the increase of intracellular calcium levels causing secretion of GLP-1.

GLP-1 is a gut-derived peptide secreted from intestinal L-cells after a meal. GLP-1 exerts profound effects in the regulation of glycaemia, stimulating glucose-dependent insulin secretion, pro-insulin gene expression and beta-cell proliferative pathways [Drucker D. J., Cell Metab (2006), 3(3): p. 153-65]. GLP-1 secretion is reduced in patients with type 2 diabetes, and this may contribute in part to the hyperglycaemia observed in these individuals [Mannucci E. et al., Diabet Med (2000), 17(10): p. 713-9]. The confirmed success of GLP-1 to lower glycaemia has led to approval of the GLP-1 receptor agonist exendin-4 (Byetta) and Liraglutide (Victoza) as well as inhibitors of the GLP-1 peptidase Dipeptidyl-peptisase-4 (DPP-4), for the treatment of patients with type 2 diabetes (T2D).

At least initially, individuals affected by T2D do not need insulin treatment since beta cells compensate by increasing their insulin production. As the disease progress, the compensatory response fails in producing insulin and maintaining normal glucose levels leading the patient to the need of a pharmaceutical treatment.

Current treatments that target either insulin resistance (metformin, thiazolidinediones) or insulin release from beta cells (sulphoylureas, exanatide) were associated to the risk of developing hypoglycaemia. Therefore, treatments based on glucose-dependent mechanisms of action to induce insulin secretion from beta-cells are needed.

Selective activation of GPR-40 and/or GPR-120 may provide potential therapeutic benefit to treat T2D and its associated conditions with minimal risk of hypoglycaemia. GPR120 is also expressed in adipocytes playing an important role in differentiation and maturation. Increased mRNA levels during adipocyte differentiation was described in in vitro models of adipogenesis as well as in human adipose tissue [Gotoh C. et al., Biochem Biophys Res Commun (2007), 354(2): p 591-7]. It was shown that GPR120 expression in human adipose tissue was significantly higher in obese individuals than controls, suggesting that the expression of GPR120 could be enhanced by the accumulation of dietary lipids. The same study revealed that GPR120-deficient HFD mice developed obesity [Ichimura A. et al., Nature (2012), 483(7389): p 350-4]. These data show that GPR120 acts as a lipid sensor and suppression of lipolysis by a GPR120 agonist would decrease the concentration of FFAs in blood, normalizing lipid levels and indeed leading to improvement in insulin resistance.

Based on clinical studies, that correlated body fat mass with lower bone density and increased fracture risk, lipids were thought to have a direct action on bone. The effects of GPR120/40 agonists were therefore tested as therapeutic molecules in bone metabolism regulation [Cornish J. et al., Endocrinology (2008), 149(11): p 5688-95].

Finally, it has been shown that GPR120 on macrophages can be activated by omega-3 fatty acids for the repression of inflammatory cytokine release. GPR120 anti-inflammatory effects are mediated by β-arrestin signalling [Oh D. Y. et al., Cell (2010), 142: p 687-98]. In vivo experiments on obese mice treated with an orally available GPR120 agonist, demonstrated the potent anti-inflammatory effects of GPR120 activation and the consequent improved glucose tolerance, decreased hyperinsulinemia, increased insulin sensitivity and decreased hepatic steatosis [Oh D. Y. et al., Nat Med (2014), 20: p 942-7].

WO2014/073904 discloses a novel compound having GPR40 receptor agonist activity that promotes insulin secretion and inhibits blood sugar rise after glucose loading, and is thereby useful for the treatment of diabetes and complications thereof, the preparation method thereof and pharmaceutical composition containing them as an active ingredient.

WO2014/209034 discloses novel biaryl derivatives as GPR120 agonists, a method for preparing the same, a pharmaceutical composition comprising the same as active components and use thereof for preventing or treating diabetes, complications of diabetes, obesity, non-alcoholic fatty liver, steatohepatitis, osteoporosis or inflammation.

US2011184031 discloses a novel phenyl compound, particularly an aralkylcarboxylic acid compound, having an agonistic activity for GPR120 and/or GPR40.

WO2016/057731 relates to novel compounds which are GPR40 agonists for the treatment of various diseases, syndromes and disorders, including Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation and eczema.

US20150274672 reports compounds as GPR120 modulators for the treatment and/or prevention of diabetes, obesity, hyperlipidaemia, inflammation and related disorders.

SUMMARY OF THE INVENTION

The aim of the present invention is to provide novel agonists of GPR120 and/or GPR40.

The present inventors have now found a new class of substituted benzenesulfonamides acting as agonists of GPR120 and/or GPR40.

These compounds are useful in the treatment of diseases or disorders modulated by said GPRs.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

The term "pharmaceutically acceptable salts" herein refers to those salts which possess the biological effectiveness and properties of the salified compound and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate, hydrogen sulphate, citrate, maleate, fumarate, trifluoroacetate, 2-naphthalenesulphonate, and para-toluenesulphonate. Further information on pharmaceutically acceptable salts can be found in Handbook of pharmaceutical salts, P. Stahl, C. Wermuth, WILEY-VCH, 127-133, 2008, herein incorporated by reference.

The term "halogen" herein refers to fluorine (F), chlorine (Cl), bromine (Br), or iodine (I).

The term "$C_1$-$C_6$ alkyl" herein refers to a branched or linear hydrocarbon containing from 1 to 6 carbon atoms. Examples of $C_1$-$C_6$ alkyl groups include but are not limited to methyl, ethyl, n-propyl, isopropyl, n-butyl, sec-butyl, isobutyl, tert-butyl, n-pentyl, n-hexyl.

The term "aryl" herein refers to aromatic mono- and poly-carbocyclic ring systems, wherein the individual carbocyclic rings in the poly-carbocyclic ring systems may be fused or attached to each other via a single bond. Suitable aryl groups include, but are not limited to, phenyl, naphthyl and biphenyl.

The term "heterocycle" herein refers to a 4-, 5-, 6-, 7- or 8-membered monocyclic ring which is saturated or unsaturated, and which consists of carbon atoms and one or more heteroatoms selected from N, O and S, and wherein the nitrogen and sulphur heteroatoms may optionally be oxidized, and the nitrogen heteroatom may optionally be quaternized. The heterocycle ring may be attached to any heteroatom or carbon atom, provided that attachment results in the creation of a stable structure. The term also includes any bicyclic system in which any of the above heterocyclic rings is fused to an aryl or another heterocycle. When the heterocycle ring is an aromatic heterocycle ring it can be defined "heteroaromatic ring".

The term "five-membered ring heterocycles" herein refers to a saturated or unsaturated ring having five ring atoms wherein 1, 2, 3 or 4 ring atoms are independently selected from N, O and S. The term also includes any bicyclic system.

Exemplary five-membered ring heterocycles are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, benzimidazole, and the like.

The term "unsaturated ring" herein refers to a ring which is partially or fully unsaturated. For example, an unsaturated monocyclic $C_6$ ring refers to cyclohexene, cyclohexadiene and benzene.

The term "substituted" herein refers to mono- or poly-substitution by a named (or undefined) substituent to the extent that such a single or multiple substitution is chemically allowed. For example, a carbocycle or heterocycle substituted with more than one substituent can have multiple substituents on the same ring atom to the extent it is chemically permitted. A ring sulphur atom in a saturated heterocycle can, for example, typically be substituted with one (—S(=O)—) or two oxo groups (—SO$_2$—).

The terms "approximately" and "about" herein refers to the range of the experimental error, which may occur in a measurement.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics of the invention are included (optional excipients may thus included).

The terms "consists of", "consisting of" are to be construed as a closed term.

DETAILED DESCRIPTION OF THE INVENTION

A first object of the present invention are compounds of formula (I):

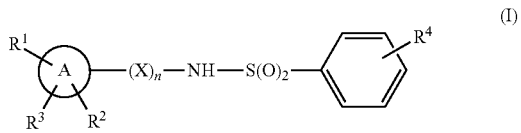

and pharmaceutically acceptable salts thereof,
wherein:
A is a mono or di-carbocyclic residue, optionally partially or totally unsaturated, comprising carbon atoms and optionally one or more heteroatoms selected from N, S or O;
$R^1$, $R^2$, $R^3$ are independently selected from the group comprising —H, -halogen, —CF$_3$, —CN, —CH$_2$CN, —OMe, —OCF$_3$, —OH, phenyl, —OPh, —OCH$_2$Ph, —OCH$_2$OMe, —OCH$_2$CN—NO$_2$, —NR'R", linear or branched C$_1$-C$_6$ alkyl, —O(CH$_2$)$_p$—S(O)$_2$Me and a five-membered ring heterocycle;

wherein R' and R" are independently —H or C$_1$-C$_4$ alkyl;

wherein phenyl and the five-membered ring heterocycle are independently unsubstituted or substituted with a group selected from the group comprising linear or branched C$_1$-C$_4$ alkyl, halogen, —OMe and —OH;

p is 1 to 4;

X is —CH$_2$ or —C(O);

n is 0, 1 or 2;

R$^4$ is —Y—C(O)OH, wherein Y is a straight chain C$_4$-C$_{18}$ hydrocarbon, saturated or unsaturated, preferably having from 6 to 10 carbon atoms;

R$^4$ is in position meta or para on the aromatic ring;

wherein when A is phenyl, n is 0, Y is a C$_4$ hydrocarbon, at least one of said R$^1$, R$^2$, R$^3$ is not hydrogen;

wherein when A is phenyl, n is 0, Y is a C$_4$ hydrocarbon, R$^1$ and R$^2$ are hydrogen, R$^3$ is not Cl in position para on the aromatic ring.

Preferably A is phenyl, naphthyl, biphenyl or a five-membered ring heterocycle having five ring atoms wherein 1, 2, 3 or 4 ring atoms are independently selected from N, O and S.

More preferably, the five-membered ring heterocycle is selected from the group comprising thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, and benzimidazole, optionally partially saturated.

According to a preferred embodiment, R$^1$, R$^2$, R$^3$ are independently selected from the group comprising —H, -halogen, —CF$_3$, —OMe, —OH, phenyl, —OPh, —OCH$_2$Ph, —OCH$_2$OMe, —OCH$_2$CN—NO$_2$, —NH$_2$, —NMe$_2$, linear or branched C$_1$-C$_6$ alkyl and —O(CH$_2$)$_p$—S(O)$_2$Me.

In an embodiment according to the invention, n is 0 or 1.

In another embodiment according to the invention, R$^4$ is in position meta on the aromatic ring.

Preferred compounds of formula (I) according to the invention are selected from:

7-(3-(N-(4-fluoro-2,6-dimethylphenyl)sulfamoyl)phenyl) heptanoic acid (1);

7-(3-(N-(2,4,6-trimethylbenzyl)sulfamoyl)phenyl)heptanoic acid (2);

7-(3-(N-(4-isopropyl-2,6-dimethylphenyl)sulfamoyl)phenyl)heptanoic acid (3);

7-(3-(N-(4-chloro-2,6-dimethylphenyl)sulfamoyl)phenyl) heptanoic acid (4);

7-(3-(N-(4-(dimethylamino)-2,6-dimethylphenyl)sulfamoyl)phenyl)heptanoic acid (5);

7-(3-(N-(2,6-dimethyl-4-(trifluoromethyl)phenyl)sulfamoyl)phenyl)heptanoic acid (6);

7-(3-(N-(4-bromo-2,6-dimethylphenyl)sulfamoyl)phenyl) heptanoic acid (7);

7-(3-(N-(4-methoxy-2,6-dimethylphenyl)sulfamoyl)phenyl) heptanoic acid (8);

7-(3-(N-(6-fluoro-4-methyl-[1,1'-biphenyl]-3-yl)sulfamoyl) phenyl)heptanoic acid (9);

7-(3-(N-(5-fluoro-3-methyl-[1,1'-biphenyl]-2-yl)sulfamoyl) phenyl)heptanoic acid (10);

6-{3-[(2,4,6-trimethylphenyl)sulfamoyl]phenyl}hexanoic acid (11);

7-(3-(N-(3,5-dimethyl-1H-pyrazol-4-yl)sulfamoyl)phenyl) heptanoic acid (12);

7-(3-(N-(2,4-dimethylthiazol-5-yl)sulfamoyl)phenyl)heptanoic acid (13);

7-(3-(N-(4,5-dimethylthiazol-2-yl)sulfamoyl)phenyl)heptanoic acid (14);

7-(3-(N-(4,5-dimethyloxazol-2-yl)sulfamoyl)phenyl)heptanoic acid (15);

7-(3-(N-(5-phenyl-1,2,4-thiadiazol-3-yl)sulfamoyl)phenyl) heptanoic acid (16);

7-(3-(N-(3-methyl-1,2,4-thiadiazol-5-yl)sulfamoyl)phenyl) heptanoic acid (17);

7-(3-(N-(5-methyl-1,3,4-thiadiazol-2-yl)sulfamoyl)phenyl) heptanoic acid (18);

7-(3-(N-(3,5-dimethylisoxazol-4-yl)sulfamoyl)phenyl)heptanoic acid (19);

7-(3-(N-(5-methyl-4H-1,2,4-triazol-3-yl)sulfamoyl)phenyl) heptanoic acid (20);

7-(3-(N-(3,5-dimethyl-4H-1,2,4-triazol-4-yl)sulfamoyl) phenyl)heptanoic acid (21);

7-(3-(N-(3-phenylisothiazol-5-yl)sulfamoyl)phenyl)heptanoic acid (22);

7-{3-[(5-hydroxynaphthalen-1-yl)sulfamoyl]phenyl}heptanoic acid (23);

7-{3-[(4-fluoro-2,6-dimethylbenzoyl)sulfamoyl]phenyl}heptanoic acid (24);

7-{4-[(4-fluoro-2,6-dimethylphenyl)sulfamoyl]phenyl}heptanoic acid (25);

7-(3-(N-(2-ethyl-2H-1,2,3-triazol-4-yl)sulfamoyl)phenyl) heptanoic acid (26);

7-(3-(N-(2-methyl-2H-tetrazol-5-yl)sulfamoyl)phenyl)heptanoic acid (27);

7-(3-(N-(4-methyl-4,5-dihydrooxazol-2-yl)sulfamoyl)phenyl)heptanoic acid (28);

7-(3-(N-(3a,4,5,6,7,7a-hexahydro-1H-benzo[d]imidazol-2yl)sulfamoyl)phenyl) heptanoic acid (29);

7-(3-(N-(3-phenylisothiazol-4-yl)sulfamoyl)phenyl)heptanoic acid (30);

7-(3-(N-(4-hydroxy-2,6-dimethylphenyl)sulfamoyl)phenyl) heptanoic acid (31);

7-(3-(N-(3,5-dimethyl-[1,1'-biphenyl]-4-yl)sulfamoyl)phenyl)heptanoic acid (32);

7-(3-(N-(2,6-dimethyl-4-phenoxyphenyl)sulfamoyl)phenyl) heptanoic acid (33);

7-(3-(N-(4-(benzyloxy)-2,6-dimethylphenyl)sulfamoyl) phenyl)heptanoic acid (34);

7-(3-(N-(2,6-dimethyl-4-(3(methylsulfonyl)propoxy)phenyl)sulfamoyl)phenyl)heptanoic acid (35).

More preferred compounds of formula (I) according to the invention are selected from:

7-(3-(N-(4-fluoro-2,6-dimethylphenyl)sulfamoyl)phenyl) heptanoic acid (1);

7-(3-(N-(2,4,6-trimethylbenzyl)sulfamoyl)phenyl)heptanoic acid (2);

7-(3-(N-(4-isopropyl-2,6-dimethylphenyl)sulfamoyl)phenyl)heptanoic acid (3);

7-(3-(N-(4-chloro-2,6-dimethylphenyl)sulfamoyl)phenyl) heptanoic acid (4);

7-(3-(N-(2,6-dimethyl-4-(trifluoromethyl)phenyl)sulfamoyl)phenyl)heptanoic acid (6);

7-(3-(N-(2,6-dimethyl-4-(trifluoromethyl)phenyl)sulfamoyl)phenyl)heptanoic acid (7)

7-(3-(N-(6-fluoro-4-methyl-[1,1'-biphenyl]-3-yl)sulfamoyl) phenyl)heptanoic acid (9);

7-(3-(N-(5-fluoro-3-methyl-[1,1'-biphenyl]-2-yl)sulfamoyl) phenyl)heptanoic acid (10);

6-{3-[(2,4,6-trimethylphenyl)sulfamoyl]phenyl}hexanoic acid (11);

7-(3-(N-(2,6-dimethyl-4-phenoxyphenyl)sulfamoyl)phenyl)
heptanoic acid (33).

As will be shown in the experimental section, the above compounds are characterized by measuring the potency in the calcium mobilization assay mediated by GPR120 and GPR40 receptors and by evaluating the secretion of GLP-1 in entero endocrine cells.

As it will be described in details in Example 36, the present inventors have found that the above compounds 1-35 are potent agonists of GPR120 and/or GPR40. The GPRs agonistic activity of all the compounds was determined in vitro by measuring the intracellular calcium levels in CHO-k1 cells stably expressing the human GPR120 or GPR40. All compounds produced concentration-dependent increases in intracellular calcium with an AC50 between 2 and 18 µM towards GPR120 and an AC50 between 5 and 13 µM towards GPR40 as shown in Table 1. These responses to each compound reflected the activation of GPR120 and GPR40 as no responses were observed in wild-type cells.

Moreover as it will be described in details in Example 37, all the above compounds were tested in vitro to evaluate the GLP-1 secretion in murine STC-1 and human NCI-H716 enteroendocrine cell lines Treatment with the compounds provided a good increase in GLP-1: the best molecules in the series were compound 9 (14.5 and 6.2 fold of increase over DMSO in STC-1 and NCI-H716, respectively) and compound 10 that showed 4.7 and 2.5 fold of increase over DMSO in STC-1 and NCI-H716, respectively (Table 1).

Thus, a second object of the present invention are the above compounds of formula (I) for use as agonists of GPR120 and/or GPR40.

Accordingly, a third object of the present invention are the above compounds for use as medicaments.

A fourth object of the present invention are the above compounds for use in the prevention and/or treatment of a disease or disorder modulated by GPR120 and/or GPR40, preferably diabetes (particularly type 2 diabetes), impaired oral glucose tolerance, insulin resistance, obesity, obesity related disorders, metabolic syndrome, dyslipidemia, elevated LDL, elevated triglycerides, obesity induced inflammation, osteoporosis and obesity related cardiovascular disorders.

A fifth object of the present invention are pharmaceutical compositions comprising the at least one of the above said compounds of formula (I) in combination with physiologically acceptable excipients.

According to an embodiment, said pharmaceutical composition contains at least one of the above compounds of formula (I) as the sole active principle(s). According to an alternative embodiment, said pharmaceutical composition contains at least one of the above compounds of formula (I) in association with at least one other active principle. According to a preferred embodiment of the invention, also in combination with the preceding embodiments, the pharmaceutical compositions may be for intravenous, intraperitoneal, inhalation, topical or oral administration.

The compounds of the invention of formula (I) are conveniently formulated in pharmaceutical compositions using conventional techniques and excipients such as those described in "Remington's Pharmaceutical Sciences Handbook" MACK Publishing, New York, 18th ed., 1990.

A sixth object of the present invention is a therapeutic method for the prevention, reduction of the risk of, amelioration and/or treatment of said disease or disorder modulated by GPR120 and/or GPR40, preferably diabetes (particularly type 2 diabetes), impaired oral glucose tolerance, insulin resistance, obesity, obesity related disorders, metabolic syndrome, dyslipidemia, elevated LDL, elevated triglycerides, obesity induced inflammation, osteoporosis and obesity related cardiovascular disorders, comprising administering the above compound of formula (I) in a subject in need thereof.

The compounds of the invention can be administered as the sole active principles or in combination with other therapeutically active compounds.

The administration of the compounds of the invention can be effected by intravenous or intraperitoneal injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day optionally divided in multiple administrations.

A seventh object of the present invention is a compound of formula (I), wherein A is phenyl $R^1$, $R^2$ and $R^3$ are hydrogen, n is 0, and $R^4$ is —$(CH_2)_4$—$C(O)OH$ for use in the prevention and/or treatment of a disease or disorder modulated by GPR120 and/or GPR40.

A eighth object of the present invention is a compound of formula (I), wherein A is phenyl, $R^1$ and $R^2$ are hydrogen, $R^3$ is Cl in position para on the aromatic ring, n is 0, and $R^4$ is —$(CH_2)_4$—$C(O)OH$ for use in the prevention and/or treatment of a disease or disorder modulated by GPR120 and/or GPR40.

Preferably, said disease or disorder is selected from diabetes (particularly type 2 diabetes), impaired oral glucose tolerance, insulin resistance, obesity, obesity related disorders, metabolic syndrome, dyslipidemia, elevated LDL, elevated triglycerides, obesity induced inflammation, osteoporosis and obesity related cardiovascular disorders.

The present invention shall be illustrated by means of the following examples which are not construed to be viewed as limiting the scope of the invention.

EXAMPLES

Synthesis of Compounds 1-35

The compounds listed in Table 1 have been synthetised following the procedures described in the following schemes and examples.

Scheme 1: Procedure A for the synthesis of the compounds

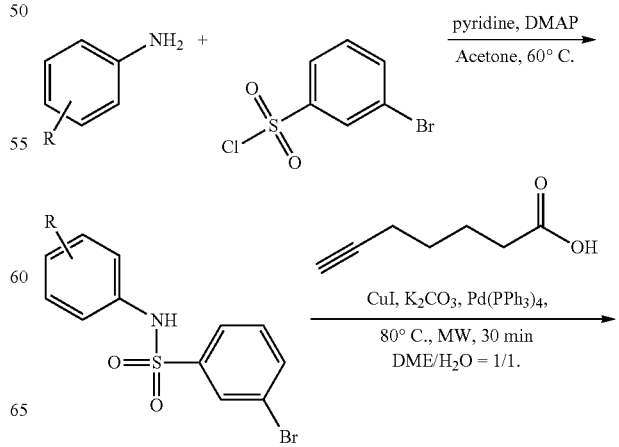

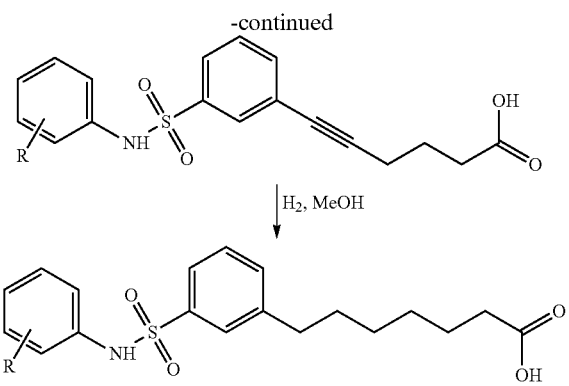

↓ H₂, MeOH

Scheme 2: Procedure B for the synthesis of the compounds

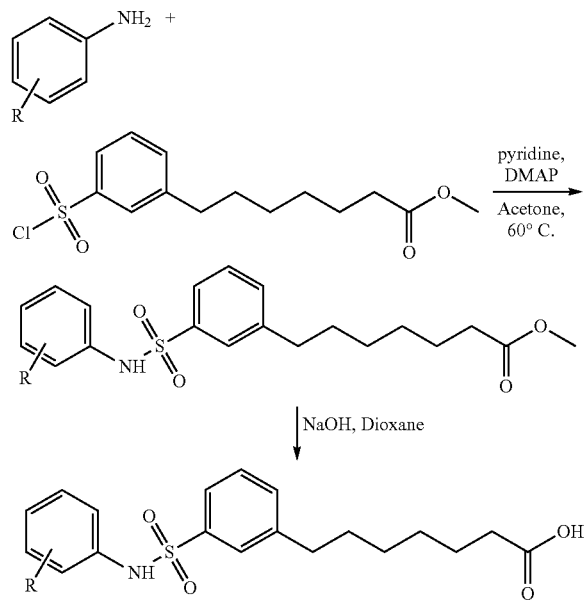

Materials and Methods

All reagents were purchased from Sigma-Aldrich, Fluorochem and Alfa Aesar and used without further purification. Nuclear magnetic resonance (NMR) spectra were recorded in the indicated solvent with tetramethylsilane (TMS) as internal standard on a Bruker Avance3 400 MHz instrument. Chemical shifts are reported in parts per million (ppm) relative to the internal standard. Abbreviations are used as follows: s=singlet, d=doublet, t=triplet, q=quartet, m=multiplet, dd=doublets of doublet, bs=broad signal. Coupling constants (J values) are given in hertz (Hz). Analytical HPLC-MS spectra were recorded on a Thermo Finnigan Surveyor coupled with a Thermo Finnigan LCQ DECA XP-PLUS apparatus and equipped with a C18 (10 μM, 4.6 mm×150 mm) Phenomenex Gemini reverse phase column. The eluent mixture consisted of 10 mM (pH 4.2) ammonium formate/formic acid buffer and acetonitrile used according the gradient from 90:10 to 10:90 at a flow rate of 0.200 mL/min. All MS experiments were performed using electrospray ionization (ESI) in positive and negative ion mode.

All reactions were monitored by thin layer chromatography (TLC) carried out on Grace Resolv Davisil silica gel plates 250 μm thick, 60 F254, visualized by using UV (254 nm) or stains such as KMnO4, p-anisaldehyde, and ceric ammonium molybdate (CAM). Chromatographic purifications were carried out on silica gel columns with Grace Resolv Davisil silica 60. All organic solutions were dried over anhydrous $Na_2SO_4$ or $MgSO_4$ and concentrated on a rotary evaporator. All compounds used for biological assays are at least of 98% purity based on HPLC analytical results monitored with 220 and 254 nm wavelengths, unless otherwise noted.

Semi-preparative purifications were performed by HPLC-UV equipped with pump Gilson 321, UV-cell Gilson 152, Fraction collector Gilson 202, System Interface Gilson 506C. Column: Phenomenex Gemini-NX AXIA 150×21.2 mm, 5 μm, 110 Å.

General Procedure

Procedure A

Synthesis of methyl 7-(3-(N-(4-fluoro-2,6-dimethylphenyl)sulfamoyl)phenyl) heptanoate (Intermediate a)

4-fluoro-2,6-dimethylaniline (74.2 mg, 0.533 mmol) was dissolved in anhydrous acetone (1.5 mL). Pyridine (0.65 mL, 8.0 mmol), DMAP (130 mg, 1.07 mmol) and methyl 7-(3-(chlorosulfonyl)phenyl)heptanoate (170 mg, 0.533 mmol) were added, and the mixture was refluxed overnight. The mixture was concentrated under reduced pressure, and the residue was purified by semi-preparative HPLC (gradient elution with water/acetonitrile containing trifluoroacetic acid), to afford the product as a colorless oil (66 mg, Y=29%). MS (ESI⁺) m/z: 422.2 [M+H]⁺.

Example 1

Synthesis of 7-(3-(N-(4-fluoro-2,6-dimethylphenyl)sulfamoyl)phenyl)heptanoic Acid (1)

Methyl 7-(3-(N-(4-fluoro-2,6-dimethylphenyl)sulfamoyl)phenyl) heptanoate (intermediate a, 66 mg, 0.16 mmol) was dissolved in dioxane (3 mL). NaOH 2M aq (1.2 mL, 2.4 mmol) was added, and the mixture was stirred at RT. Upon complete conversion (2 hours; HPLC-UV-MS monitoring), the mixture was concentrated under reduced pressure. The residue was dissolved in ethyl acetate (5 mL) and washed with HCl 0.3M aq (3×5 mL) and brine (3×5 mL). The organic layer was dried ($Na_2SO_4$) and concentrated to afford 1 as a white solid (56 mg, Y=88%). ¹H-NMR (CHLOROFORM-d): δ 1.22-1.43 (m, 4H) 1.51-1.67 (m, 4H) 1.99 (s, 6H) 2.35 (t, J=7.02 Hz, 2H) 2.62 (t, J=7.11 Hz, 2H) 6.24 (br s, 1H) 6.71 (d, J=9.2 Hz, 2H) 7.34-7.40 (m, 2H) 7.46-7.54 (m, 2H). MS (ESI⁺) m/z: 408.2 [M+H]⁺

Procedure B

Synthesis of 3-bromo-N-(2,4,6-trimethylbenzyl)benzenesulfonamide (Intermediate b)

3-Bromo-N-(2,4,6-trimethylbenzyl)benzenesulfonamide was obtained as described in Procedure A (221 mg, Y=56%), by reaction of mesitylmethanamine (160 mg, 1.07 mmol) with 3-bromobenzenesulfonyl chloride (271 mg, 1.07 mmol). MS (ESI⁺) m/z: 390.1 [M+Na]⁺.

Synthesis of 7-(3-(N-(2,4,6-trimethylbenzyl)sulfamoyl)phenyl)hept-6-ynoic acid (Intermediate c)

3-bromo-N-(2,4,6-trimethylbenzyl)benzenesulfonamide (intermediate b, 302 mg, 0.820 mmol), potassium carbonate (397 mg, 2.87 mmol), tetrakis(triphenylphosphoranyl)palladium (95 mg, 0.082 mmol) and copper(I) iodide (15.63 mg, 0.082 mmol) were suspended in a DME/H$_2$O mixture (1/1 vol.) (2 mL). The resulting mixture was stirred under nitrogen for 5 minutes, and hept-6-ynoic acid (0.212 mL, 1.64 mmol) was added. The mixture was irradiated with microwaves for 1 h at 80° C. After removing the DME under reduced pressure, the residue was taken with AcOEt (15 mL) and washed with HCl aq 2M (2×10 mL) and brine (2×10 mL). The organic layer was concentrated under reduced pressure and the residue was purified by semi-preparative HPLC-UV, to afford the product as a colorless oil (206 mg, Y=61%). MS (ESI$^+$) m/z: 279.1 [M+H]$^+$.

Example 2

Synthesis of 7-(3-(N-(2,4,6-trimethylbenzyl)sulfamoyl)phenyl)heptanoic Acid (2)

Palladium 10% wt on carbon (273 mg, 0.256 mmol) was suspended in methanol (10 mL), and 7-(3-(N-(2,4,6-trimethylbenzyl)sulfamoyl)phenyl)hept-6-ynoic acid (intermediate c, 530 mg, 1.28 mmol) was added. Hydrogen was bubbled through the mixture for 15 minutes, whereupon the mixture was allowed to stir at RT for 1 hour under hydrogen atmosphere. At this time, conversion was complete (HPLC-UV-MS). The mixture was filtered through a pad of Celite® and washed with methanol (30 mL). The mixture was concentrated under reduced pressure and the residue was purified by semi preparative HPLC-UV, to afford the product as a colorless oil (390 mg, Y=73%). $^1$H NMR (300 MHz, CHLOROFORM-d) δ ppm 1.20 (d, J=7.03 Hz, 6H) 1.27-1.40 (m, 4H) 1.48-1.70 (m, 4H) 1.99 (s, 6H) 2.35 (t, J=7.58 Hz, 2H) 2.60 (t, J=7.58 Hz, 2H) 2.79 (spt, J=7.03 Hz, 1H) 6.21 (br s, 1H) 6.85 (s, 2H) 7.31-7.43 (m, 2H) 7.48 (s, 1H) 7.53-7.64 (m, 1H). MS (ESI$^+$) m/z: 440.2 [M+Na]$^+$.
Synthesis of Compounds 3-35

Example 3

Synthesis of 7-(3-(N-(4-isopropyl-2,6-dimethylphenyl)sulfamoyl)phenyl) heptanoic Acid (3)

Starting from 4-isopropyl-2,6-dimethylaniline hydrochloride salt (31 mg, 0.16 mmol), methyl 7-(3-(N-(4-isopropyl-2,6-dimethylphenyl)sulfamoyl)phenyl)heptanoate was obtained (25 mg, Y=36%) as described in Procedure A. MS (ESI$^+$) m/z: 446.3 [M+H]$^+$.

Compound 3 was then obtained by hydrolysis of the ester derivative (25 mg, 0.056 mmol) as described for compound 1, as a yellow waxy solid (22 mg, Y=91%). $^1$H NMR (300 MHz, CHLOROFORM-d) δ ppm 1.20 (d, J=7.03 Hz, 6H) 1.27-1.40 (m, 4H) 1.48-1.70 (m, 4H) 1.99 (s, 6H) 2.35 (t, J=7.58 Hz, 2H) 2.60 (t, J=7.58 Hz, 2H) 2.79 (spt, J=7.03 Hz, 1H) 6.21 (br s, 1H) 6.85 (s, 2H) 7.31-7.43 (m, 2H) 7.48 (s, 1H) 7.53-7.64 (m, 1H) MS (ESI$^+$) m/z: 432.2 [M+H]$^+$.

Example 4

Synthesis of 7-(3-(N-(4-chloro-2,6-dimethylphenyl)sulfamoyl)phenyl)heptanoic Acid (4)

Starting from 4-chloro-2,6-dimethylaniline (1.50 g, 9.64 mmol), 3-bromo-N-(4-chloro-2,6-dimethylphenyl)benzenesulfonamide was synthesized as described in Procedure B, affording a mixture of mono- and di-sulfonamide, which by hydrolysis with NaOH aq/Dioxane was completely converted to the mono-sulfonamide (3.00 g, Y=83%). MS (ESI$^+$) m/z: 395.9 [M+Na]$^+$.

The sulfonamide (2.90 g, 7.74 mmol) was then coupled with hept-6-ynoic acid (2.00 mL, 15.5 mmol) as described in Procedure B, to afford 7-(3-(N-(4-chloro-2,6-dimethylphenyl)sulfamoyl)phenyl)hept-6-ynoic acid (980 mg, Y=32%). MS (ESI$^+$) m/z: 420.1 [M+H]$^+$.

Compound 4 was then obtained by reduction of the alkyne derivative (980 mg, 2.33 mmol) as described for compound 2, as a white solid (158 mg, Y=16%). $^1$H NMR (300 MHz, CHLOROFORM-d) δ ppm 1.27-1.43 (m, 4H) 1.51-1.69 (m, 4H) 1.99 (s, 6H) 2.37 (t, J=7.31 Hz, 2H) 2.62 (t, J=7.59 Hz, 2H) 6.56 (s, 1H) 7.01 (s, 2H) 7.37-7.41 (m, 2H) 7.48-7.57 (m, 2H). MS (ESI$^+$) m/z 446.1 [M+Na]$^+$.

Example 5

Synthesis of 7-(3-(N-(4-(dimethylamino)-2,6-dimethylphenyl)sulfamoyl)phenyl) heptanoic Acid (5)

Starting from N1,N1,3,5-tetramethylbenzene-1,4-diamine (19.7 mg, 0.120 mmol), ethyl 7-(3-(N-(4-(dimethylamino)-2,6-dimethylphenyl)sulfamoyl)phenyl)heptanoate was obtained (21 mg, Y=38%) as described in Procedure A. MS (ESI$^+$) m/z: 461.3 [M+H]$^+$.

Compound 5 was then obtained by hydrolysis of the ester derivative (21 mg, 0.046 mmol) as described for compound 1, as a beige solid (19 mg, Y=97%). $^1$H NMR (300 MHz, CHLOROFORM-d) δ ppm 1.26-1.40 (m, 4H) 1.48-1.69 (m, 4H) 1.95 (s, 6H) 2.34 (t, J=7.30 Hz, 2H) 2.61 (t, J=7.58 Hz, 2H) 2.90 (s, 6H) 6.01 (s, 1H) 6.37 (s, 2H) 7.30-7.41 (m, 2H) 7.47-7.61 (m, 2H). MS (ESI$^+$) m/z: 433.2 [M+H]$^+$.

Example 6

Synthesis of 7-(3-(N-(2,6-dimethyl-4-(trifluoromethyl)phenyl)sulfamoyl)phenyl) heptanoic Acid (6)

Starting from 2,6-dimethyl-4-(trifluoromethyl)aniline hydrochloride salt (34 mg, 0.15 mmol), ethyl 7-(3-(N-(2,6-dimethyl-4-(trifluoromethyl)phenyl)sulfamoyl)phenyl) heptanoate was obtained (11.4 mg, Y=16%) as described in Procedure A. MS (ESI$^+$) m/z: 486.2 [M+H]$^+$.

Compound 6 was then obtained by hydrolysis of the ester derivative (5.7 mg, 0.012 mmol) as described for compound 1, as a beige waxy solid (2.0 mg, Y=37%). $^1$H NMR (300 MHz, CHLOROFORM-d) δ ppm 1.29-1.43 (m, 4H) 1.53-1.70 (m, 4H) 2.17 (s, 6H) 2.41 (t, J=7.36 Hz, 2H) 2.64 (t, J=7.44 Hz, 2H) 6.47 (s, 1H) 7.13-7.42 (m, 4H) 7.46-7.70 (m, 2H). MS (ESI$^+$) m/z: 480.2 [M+Na]$^+$.

Example 7

Synthesis of 7-(3-(N-(4-bromo-2,6-dimethylphenyl) sulfamoyl)phenyl)heptanoic Acid (7)

Starting from 4-bromo-2,6-dimethylaniline (24 mg, 0.12 mmol), ethyl 7-(3-(N-(4-bromo-2,6-dimethylphenyl)sulfamoyl)phenyl)heptanoate was obtained (9.5 mg, Y=16%) as described in Procedure A. MS (ESI$^+$) m/z: 496.1 [M+H]$^+$.

Compound 7 was then obtained by hydrolysis of the ester derivative (8.5 mg, 0.017 mmol) as described for compound 1, as a white solid (8.0 mg, Y=99%). $^1$H NMR (300 MHz, CHLOROFORM-d) δ ppm 1.20-1.44 (m, 4H) 1.48-1.69 (m, 4H) 1.98 (s, 6H) 2.36 (t, J=7.30 Hz, 2H) 2.62 (t, J=7.58 Hz, 2H) 6.29 (br s, 1H) 7.16 (s, 2H) 7.33-7.42 (m, 2H) 7.46-7.55 (m, 2H). MS (ESI$^+$) m/z 468.2 [M+H]$^+$.

Example 8

Synthesis of 7-(3-(N-(4-methoxy-2,6-dimethylphenyl)sulfamoyl)phenyl) heptanoic Acid (8)

4-Amino-3,5-xylenol (50 mg, 0.36 mmol) and sodium 2-methylpropan-2-olate (52 mg, 0.55 mmol) were dissolved in dry DMF (1 ml) under Argon atmosphere. Iodomethane (0.021 ml, 0.33 mmol) was added, and the mixture was stirred overnight. DCM (20 mL) was added and the solution was washed with NaOH aq 1M (2×15 mL) and brine (2×15 mL). The organic layer was dried over Na$_2$SO$_4$, filtered and concentrated under reduced pressure. The residue was purified over silica (Hexane/AcOEt 2/1) to afford 4-methoxy-2,6-dimethylaniline (24 mg, Y=43%). MS (ESI$^+$) m/z: 152.1 [M+H]$^+$.

Starting from 4-methoxy-2,6-dimethylaniline (24 mg, 0.16 mmol), methyl 7-(3-(N-(4-methoxy-2,6-dimethylphenyl)sulfamoyl)phenyl)heptanoate was obtained (12 mg, Y=17%) as described in Procedure A. MS (ESI$^+$) m/z: 456.2 [M+Na]$^+$.

The ester derivative (12 mg, 0.028 mmol) was hydrolized as described in procedure A, to afford compound 8 as an orange oil (11 mg, Y=95%). $^1$H NMR (300 MHz, CHLOROFORM-d) δ ppm 1.22-1.36 (m, 4H) 1.49-1.66 (m, 4H) 1.97 (s, 6H) 2.30 (t, J=6.76 Hz, 2H) 2.61 (t, J=7.58 Hz, 2H) 3.75 (s, 3H) 6.53 (s, 1H) 7.31-7.39 (m, 3H) 7.46-7.57 (m, 3H). MS (ESI$^+$) m/z 442.2 [M+Na]$^+$.

Example 9

Synthesis of 7-(3-(N-(6-fluoro-4-methyl-[1,1'-biphenyl]-3-yl)sulfamoyl)phenyl) heptanoic Acid (9)

(1,1'-bis(diphenylphosphino)ferrocene)-dichloropalladium(II) (234 mg, 0.286 mmol), phenylboronic acid (907 mg, 7.44 mmol) and 5-bromo-4-fluoro-2-methylaniline (1.17 g, 5.72 mmol) were dissolved in DME (10 ml). Sodium carbonate aq 2M (5.7 mL, 11 mmol) was added, and the mixture was irradiated with microwaves for 2 h at 120° C. After removing the DME under reduced pressure, the residue was taken with AcOEt (15 mL) and washed with brine (2×10 mL). The organic layer was concentrated under reduced pressure and the residue was purified by semipreparative HPLC-UV, to afford 6-fluoro-4-methyl-[1,1'-biphenyl]-3-amine (812 mg, Y=70%) as a dark oil. MS (ESI$^+$) m/z: 202.1 [M+H]$^+$.

Starting from 6-fluoro-4-methyl-[1,1'-biphenyl]-3-amine (751 mg, 3.73 mmol), 3-bromo-N-(6-fluoro-4-methyl-[1,1'-biphenyl]-3-yl)benzenesulfonamide was synthesized as described in Procedure B, affording a mixture of mono- and di-sulfonamide, which by hydrolysis with NaOH aq/Dioxane was completely converted to the mono-sulfonamide (1.41 g, Y=89%). MS (ESI$^+$) m/z: 442.0 [M+Na]$^+$.

The sulfonamide (1.03 g, 2.46 mmol) was then coupled with hept-6-ynoic acid (0.63 mL, 4.92 mmol) as described in Procedure B, to afford 7-(3-(N-(6-fluoro-4-methyl-[1,1'-biphenyl]-3-yl)sulfamoyl)phenyl)hept-6-ynoic acid (290 mg, Y=25%). MS (ESI$^+$) m/z: 466.2 [M+H]$^+$.

Compound 9 was then obtained by reduction of the alkyne derivative (290 mg, 0.623 mmol) as described for compound 2, as a white solid (235 mg, Y=80%). $^1$H NMR (300 MHz, CHLOROFORM-d) δ ppm 1.20-1.33 (m, 4H) 1.47-1.59 (m, 4H) 2.01 (s, 3H) 2.31 (t, J=7.34 Hz, 2H) 2.58 (t, J=7.56 Hz, 2H) 6.88 (d, J=10.96 Hz, 1H) 7.00 (s, 1H) 7.27 (d, J=7.45 Hz, 1H) 7.32-7.43 (m, 7H) 7.51-7.60 (m, 2H). MS (ESI$^+$) m/z: 470.2 [M+H]$^+$.

Example 10

Synthesis of 7-(3-(N-(5-fluoro-3-methyl-[1,1'-biphenyl]-2-yl)sulfamoyl)phenyl) heptanoic Acid (10)

Starting from 2-bromo-4-fluoro-6-methylaniline (360 mg, 1.76 mmol), 5-fluoro-3-methyl-[1,1'-biphenyl]-2-amine (336 mg, Y=94%) was synthesized by Suzuki coupling as described for compound 9. MS (ESI$^+$) m/z: 202.1 [M+H]$^+$.

Starting from 5-fluoro-3-methyl-[1,1'-biphenyl]-2-amine (266 mg, 1.32 mmol), 3-bromo-N-(5-fluoro-3-methyl-[1,1'-biphenyl]-2-yl)benzenesulfonamide was synthesized as described in Procedure B, affording a mixture of mono- and di-sulfonamide, which by hydrolysis with NaOH aq/Dioxane was completely converted to the mono-sulfonamide (540 mg, Y=97%). MS (ESI$^+$) m/z: 442.1 [M+Na]$^+$.

The sulfonamide (540 mg, 1.28 mmol) was then coupled with hept-6-ynoic acid (0.33 mL, 2.57 mmol) as described in Procedure B, to afford 7-(3-(N-(5-fluoro-3-methyl-[1,1'-biphenyl]-2-yl)sulfamoyl)phenyl)hept-6-ynoic acid (290 mg, Y=41%). MS (ESI$^+$) m/z: 466.2 [M+H]$^+$.

Compound 10 was then obtained by reduction of the alkyne derivative (250 mg, 0.537 mmol) as described for compound 2, as a white solid (75 mg, Y=30%). $^1$H NMR (300 MHz, CHLOROFORM-d) δ ppm 1.24-1.42 (m, 4H) 1.51 (tt, J=7.34, 7.34 Hz, 2H) 1.64 (tt, J=7.23, 7.23 Hz, 2H) 2.36 (t, J=7.34 Hz, 2H) 2.48 (t, J=7.67 Hz, 2H) 2.52 (s, 3H) 6.65 (s, 1H) 6.70 (dd, J=8.66, 2.96 Hz, 1H) 6.78 (d, J=6.58 Hz, 2H) 6.95-7.28 (m, 8H). MS (ESI$^+$) m/z: 470.2 [M+H]$^+$.

Example 11

Synthesis of 6-{3-[(2,4,6-trimethylphenyl)sulfamoyl]phenyl}hexanoic Acid (11)

Starting from 2,4,6-trimethylaniline (15 mg, 0.16 mmol), methyl 6-{3-[(2,4,6-trimethylphenyl)sulfamoyl]phenyl}hexanoate was obtained (20 mg, Y=34%) as described in Procedure A. MS (ESI$^+$) m/z: 404.4 [M+H]$^+$.

Compound 11 was then obtained by hydrolysis of the ester derivative (20 mg, 0.053 mmol) as described for compound 1, as a beige solid (12 mg, Y=61%). $^1$H NMR (300 MHz, DMSO-d) δ ppm 1.21-1.32 (m, 2H) 1.42-1.65 (m, 4H) 1.81-2.05 (s, 6H) 2.11-2.23 (m, 5H) 2.65-2.71 (m, 2H) 6.84 (s, 2H) 7.41 (s, 1H) 7.52-7.61 (m, 3H) 9.1 (br s, 1H) 11.9 (br s, 1H). MS (ESI$^+$) m/z: 390.3 [M+H]$^+$.

Example 12

Synthesis of 7-(3-(N-(3,5-dimethyl-1H-pyrazol-4-yl)sulfamoyl)phenyl)heptanoic Acid (12)

Starting from 3,5-dimethyl-1H-pyrazol-4-amine (300 mg, 2.70 mmol), methyl 7-(3-(N-(3,5-dimethyl-1H-pyrazol-4-yl)sulfamoyl)phenyl)heptanoate was obtained (380 mg, Y=35%) as described in Procedure A. MS (ESI$^+$) m/z: 394.2 [M+H]$^+$.

Compound 12 was then obtained by hydrolysis of the ester derivative (380 mg, 0.966 mmol) as described for compound 1, as a white solid (257 mg, Y=70%). $^1$H NMR (300 MHz, CHLOROFORM-d) δ ppm 1.30-1.45 (m, 4H) 1.52-1.71 (m, 4H) 2.14 (s, 6H) 2.31 (t, J=7.23 Hz, 2H) 2.66

(t, J=7.41 Hz, 2H) 7.02 (s, 1H) 7.37-7.44 (m, 2H) 7.50-7.66 (m, 2H). MS (ESI+) m/z: 380.3 [M+H]+.

Example 13

Synthesis of 7-(3-(N-(2,4-dimethylthiazol-5-yl)sulfamoyl)phenyl)heptanoic Acid (13)

Starting from 2,4-dimethylthiazol-5-amine (250 mg, 1.95 mmol), methyl 7-(3-(N-(2,4-dimethylthiazol-5-yl)sulfamoyl)phenyl)heptanoate was obtained (372 mg, Y=46%) as described in Procedure A. MS (ESI+) m/z: 411.2 [M+H]+.

Compound 13 was then obtained by hydrolysis of the ester derivative (372 mg, 0.907 mmol) as described for compound 1, as a white solid (257 mg, Y=71%). $^1$H NMR (300 MHz, CHLOROFORM-d) δ ppm 1.28-1.41 (m, 4H) 1.50-1.72 (m, 4H) 2.06 (s, 3H) 2.27 (s, 3H) 2.34 (t, J=7.26 Hz, 2H) 2.71 (t, J=7.37 Hz, 2H) 6.94 (s, 1H) 7.12-7.31 (m, 2H) 7.48-7.56 (m, 2H). MS (ESI+) m/z: 397.2 [M+H]+.

Example 14

Synthesis of 7-(3-(N-(4,5-dimethylthiazol-2-yl)sulfamoyl)phenyl)heptanoic Acid (14)

Starting from 4,5-dimethylthiazol-2-amine (15 mg, 0.12 mmol), ethyl 7-(3-(N-(4,5-dimethylthiazol-2-yl)sulfamoyl) phenyl)heptanoate was obtained (17 mg, Y=35%) as described in Procedure A. MS (ESI+) m/z: 425.2 [M+H]+.

Compound 14 was then obtained by hydrolysis of the ester derivative (17 mg, 0.040 mmol) as described for compound 1, as a white solid (4.3 mg, Y=27%). $^1$H NMR (300 MHz, CHLOROFORM-d) δ ppm 1.05-1.43 (m, 4H) 1.53-1.72 (m, 4H) 2.13 (s, 6H) 2.30 (t, J=6.49 Hz, 2H) 2.68 (t, J=7.03 Hz, 2H) 7.06 (s, 1H) 7.30-7.37 (m, 2H) 7.68-7.73 (m, 2H). MS (ESI+) m/z: 397.1 [M+H]+.

Example 15

Synthesis of 7-(3-(N-(4,5-dimethyloxazol-2-yl)sulfamoyl)phenyl)heptanoic Acid (15)

Starting from 4,5-dimethyloxazol-2-amine (13.5 mg, 0.120 mmol), ethyl 7-(3-(N-(4,5-dimethyloxazol-2-yl)sulfamoyl)phenyl)heptanoate was obtained (18 mg, Y=37%) as described in Procedure A. MS (ESI+) m/z: 409.2 [M+H]+.

Compound 15 was then obtained by hydrolysis of the ester derivative (3 mg, 7 μmol) as described for compound 1, as an orange waxy solid (2 mg, Y=71%). $^1$H NMR (300 MHz, CHLOROFORM-d) δ ppm 1.07-1.44 (m, 4H) 1.56-1.72 (m, 7H) 1.99 (s, 3H) 2.28 (t, J=6.76 Hz, 2H) 2.61 (t, J=6.94 Hz, 2H) 6.97 (s, 1H) 7.28-7.34 (m, 2H) 7.56-7.71 (m, 2H). MS (ESI+) m/z: 381.2 [M+H]+.

Example 16

Synthesis of 7-(3-(N-(5-phenyl-1,2,4-thiadiazol-3-yl)sulfamoyl)phenyl)heptanoic Acid (16)

Starting from 5-phenyl-1,2,4-thiadiazol-3-amine (17 mg, 0.094 mmol), methyl 7-(3-(N-(5-phenyl-1,2,4-thiadiazol-3-yl)sulfamoyl)phenyl)heptanoate was obtained (7.5 mg, Y=17%) as described in Procedure A. MS (ESI+) m/z: 460.2 [M+H]+.

Compound 16 was then obtained by hydrolysis of the ester derivative (2.5 mg, 5.4 μmol) as described for compound 1, as a white solid (2.3 mg, Y=94%). $^1$H NMR (300 MHz, CHLOROFORM-d) δ ppm 1.12-1.45 (m, 4H) 1.55-1.68 (m, 4H) 2.21 (t, J=7.01 Hz, 2H) 2.48 (t, J=6.90 Hz, 2H) 7.03 (s, 1H) 7.39-7.70 (m, 5H) 7.84-7.98 (m, 4H). MS (ESI+) m/z: 446.2 [M+H]+.

Example 17

Synthesis of 7-(3-(N-(3-methyl-1,2,4-thiadiazol-5-yl)sulfamoyl)phenyl)heptanoic Acid (17)

Starting from 3-methyl-1,2,4-thiadiazol-5-amine (14 mg, 0.12 mmol) methyl 7-(3-(N-(3-methyl-1,2,4-thiadiazol-5-yl)sulfamoyl)phenyl)heptanoate was obtained (8.1 mg, Y=16%) as described in Procedure A. MS (ESI+) m/z: 398.2 [M+H]+.

Compound 17 was then obtained by hydrolysis of the ester derivative (2.7 mg, 6.8 μmol) as described for compound 1, as a yellow waxy solid (0.6 mg, Y=23%). $^1$H NMR (300 MHz, CHLOROFORM-d) δ ppm 1.10-1.46 (m, 4H) 1.55-1.73 (m, 4H) 2.11 (s, 3H) 2.31 (t, J=6.91 Hz, 2H) 2.60 (t, J=7.06 Hz, 2H) 6.88 (br s, 1H) 7.30-7.35 (m, 2H) 7.54-7.70 (m, 2H). MS (ESI+) m/z: 384.2 [M+H]+.

Example 18

Synthesis of 7-(3-(N-(5-methyl-1,3,4-thiadiazol-2-yl)sulfamoyl)phenyl)heptanoic Acid (18)

Starting from 5-methyl-1,3,4-thiadiazol-2-amine (14 mg, 0.12 mmol) methyl 7-(3-(N-(5-methyl-1,3,4-thiadiazol-2-yl)sulfamoyl)phenyl)heptanoate was obtained (12 mg, Y=25%) as described in Procedure A. MS (ESI+) m/z: 398.2 [M+H]+.

Compound 18 was then obtained by hydrolysis of the ester derivative (1.5 mg, 3.8 μmol) as described for compound 1, as a white solid (1.3 mg, Y=90%). $^1$H NMR (300 MHz, CHLOROFORM-d) δ ppm 1.11-1.49 (m, 4H) 1.56-1.74 (m, 4H) 2.28 (t, J=6.86 Hz, 2H) 2.53 (s, 3H) 2.62 (t, J=7.00 Hz, 2H) 7.02 (s, 1H) 7.36-7.47 (m, 2H) 7.64-7.74 (m, 2H). MS (ESI+) m/z: 384.1 [M+H]+.

Example 19

Synthesis of 7-(3-(N-(3,5-dimethylisoxazol-4-yl) sulfamoyl)phenyl)heptanoic Acid (19)

Starting from 3,5-dimethylisoxazol-4-amine (14 mg, 0.12 mmol) methyl 7-(3-(N-(3,5-dimethylisoxazol-4-yl)sulfamoyl)phenyl)heptanoate was obtained (11 mg, Y=22%) as described in Procedure A. MS (ESI+) m/z: 395.2 [M+H]+.

Compound 19 was then obtained by hydrolysis of the ester derivative (11 mg, 0.027 mmol) as described for compound 1, as a yellow waxy solid (4.0 mg, Y=39%). $^1$H NMR (300 MHz, CHLOROFORM-d) δ ppm 1.24-1.46 (m, 4H) 1.55-1.71 (m, 4H) 1.82 (s, 3H) 2.06 (s, 3H) 2.36 (t, J=7.03 Hz, 3H) 2.67 (t, J=7.58 Hz, 3H) 7.37-7.45 (m, 2H) 7.48-7.53 (m, 1H) 7.58 (s, 1H). MS (ESI+) m/z: 381.2 [M+H]+.

Example 20

Synthesis of 7-(3-(N-(5-methyl-4H-1,2,4-triazol-3-yl)sulfamoyl)phenyl)heptanoic Acid (20)

Starting from 5-methyl-4H-1,2,4-triazol-3-amine (50 mg, 0.509 mmol), methyl 7-(3-(N-(5-methyl-4H-1,2,4-triazol-3- yl)sulfamoyl)phenyl)heptanoate was obtained (77 mg, Y=40%) as described in Procedure A. MS (ESI$^+$) m/z: 381.2 [M+H]$^+$.

Compound 20 was then obtained by hydrolysis of the ester derivative (50 mg, 0.131 mmol) as described for compound 1, as a white solid (17 mg, Y=35%). $^1$H NMR (300 MHz, CHLOROFORM-d) δ ppm 1.16-1.42 (m, 4H) 1.54-1.72 (m, 4H) 2.25 (s, 3H) 2.30 (t, J=6.88 Hz, 2H) 2.58 (t, J=7.02 Hz, 2H) 7.36-7.48 (m, 3H) 7.66 (s, 1H). MS (ESI$^+$) m/z 367.1 [M+H]$^+$.

Example 21

Synthesis of 7-(3-(N-(3,5-dimethyl-4H-1,2,4-triazol-4-yl)sulfamoyl)phenyl)heptanoic Acid (21)

Starting from 3,5-dimethyl-4H-1,2,4-triazol-4-amine (40 mg, 0.357 mmol), methyl 7-(3-(N-(3,5-dimethyl-4H-1,2,4-triazol-4-yl)sulfamoyl)phenyl)heptanoate was obtained (60 mg, Y=43%) as described in Procedure A. MS (ESI$^+$) m/z 395.2 [M+H]$^+$.

Compound 21 was then obtained by hydrolysis of the ester derivative (60 mg, 0.152 mmol) as described for compound 1, as a white solid (23 mg, Y=40%). $^1$H NMR (300 MHz, CHLOROFORM-d) δ ppm 1.20-1.45 (m, 4H) 1.56-1.72 (m, 4H) 2.44 (s, 6H) 2.32 (t, J=6.90 Hz, 2H) 2.59 (t, J=7.06 Hz, 2H) 7.35-7.43 (m, 2H) 7.73-7.81 (m, 2H). MS (ESI$^+$) m/z: 381.1 [M+H]$^+$.

Example 22

Synthesis of 7-(3-(N-(3-phenylisothiazol-5-yl)sulfamoyl)phenyl)heptanoic Acid (22)

Starting from 3-phenylisothiazol-5-amine (22 mg, 0.12 mmol) methyl 7-(3-(N-(3-phenylisothiazol-5-yl)sulfamoyl) phenyl)heptanoate was obtained (11 mg, Y=20%) as described in Procedure A. MS (ESI$^+$) m/z: 459.2 [M+H]$^+$.

Compound 22 was then obtained by hydrolysis of the ester derivative (11 mg, 0.025 mmol) as described for compound 1, as a beige solid (6.0 mg, Y=53%). $^1$H NMR (300 MHz, CHLOROFORM-d) δ ppm 1.15-1.43 (m, 4H) 1.49-1.73 (m, 4H) 2.34 (t, J=7.03 Hz, 2H) 2.65 (t, J=7.03 Hz, 2H) 7.08 (s, 1H) 7.35-7.42 (m, 5H) 7.68-7.88 (m, 4H). MS (ESI$^+$) m/z: 445.2 [M+H]$^+$.

Example 23

Synthesis of 7-{3-[(5-hydroxynaphthalen-1-yl)sulfamoyl]phenyl}heptanoic Acid (23)

Starting from 5-aminonaphthalen-1-ol (24 mg, 0.15 mmol) methyl 7-{3-[(5-hydroxynaphthalen-1-yl)sulfamoyl] phenyl}heptanoatemethyl was obtained (34 mg, Y=51%) as described in Procedure A. MS (ESI$^+$) m/z: 442.3 [M+H]$^+$.

Compound 23 was then obtained by hydrolysis of the ester derivative (3.2 mg, 8.4 µmol) as described for compound 1, as a waxy yellow solid (2.2 mg, Y=71%). $^1$H NMR (300 MHz, METHANOL-d) δ ppm 1.11-1.20 (m, 2H) 1.22-1.40 (m, 5H) 1.55-1.78 (m, 2H) 2.21-2.41 (m, 2H) 2.43-2.56 (m, 2H) 6.73-6.74 (m, 1H) 7.04-7.09 (m, 1H) 7.19-7.22 (m, 1H) 7.28-7.34 (m, 5H) 7.53-7.54 (m, 1H) 8.09-8.11 (m, 1H). MS (ESI$^+$) m/z: 428.4 [M+H]$^+$.

Example 24

Synthesis of 7-{3-[(4-fluoro-2,6-dimethylbenzoyl) sulfamoyl]phenyl}heptanoic Acid (24)

Starting from 4-fluoro-2,6-dimethylbenzamide (18 mg, 0.11 mmol) methyl 7-{3-[(4-fluoro-2,6-dimethylbenzoyl) sulfamoyl]phenyl}heptanoate was obtained (13 mg, Y=26%) as described in Procedure A in which Pyridine was replaced with Sodium hydride and the reaction was performed in dry DMF. MS (ESI$^+$) m/z: 450.4 [M+H]$^+$.

Compound 24 was then obtained by hydrolysis of the ester derivative (3.9 mg, 8.6 µmol) as described for compound 1, as a yellow waxy solid (3.3 mg, Y=88%). $^1$H-NMR (CHLOROFORM-d): δ 1.20-1.43 (m, 4H) 1.53-1.57 (m, 4H) 1.90 (s, 6H) 2.34 (t, J=7.03 Hz, 2H) 2.54 (t, J=7.08 Hz, 2H) 6.21 (br s, 1H) 6.67 (d, J=9.2 Hz, 2H) 7.33-7.41 (m, 2H) 7.47-7.54 (m, 2H). MS (ESI$^+$) m/z: 436.5 [M+Na]$^+$.

Example 25

Synthesis of 7-{4-[(4-fluoro-2,6-dimethylphenyl) sulfamoyl]phenyl}heptanoic Acid (25)

Starting from 4-fluoro-2,6-dimethylaniline (74.2 mg, 0.533 mmol) methyl 7-{4-[(4-fluoro-2,6-dimethylphenyl) sulfamoyl]phenyl}heptanoate was obtained (81 mg, Y=36%) as described in Procedure A but starting from methyl 7-[4-(chlorosulfonyl)phenyl]heptanoate. MS (ESI$^+$) m/z: 422.4 [M+H]$^+$.

Compound 25 was then obtained by hydrolysis of the ester derivative as described for compound 1 as a brown waxy solid (71 mg, Y=91%). $^1$H-NMR (CHLOROFORM-d): δ 1.21-1.45 (m, 4H) 1.50-1.59 (m, 4H) 1.98 (s, 6H) 2.37 (t, J=7.02 Hz, 2H) 2.63 (t, J=7.11 Hz, 2H) 6.25 (br s, 1H) 6.69 (d, J=9.2 Hz, 2H) 7.32-7.38 (m, 2H) 7.45-7.54 (m, 2H). MS (ESI$^+$) m/z: 408.3 [M+H]$^+$.

Example 26

Synthesis of 7-(3-(N-(2-ethyl-2H-1,2,3-triazol-4-yl) sulfamoyl)phenyl)heptanoic Acid (26)

Starting from 2-ethyl-2H-1,2,3-triazol-4-amine (17 mg, 0.15 mmol) methyl 7-(3-(N-(2-ethyl-2H-1,2,3-triazol-4-yl) sulfamoyl)phenyl)heptanoate was obtained (16 mg, Y=26%) as described in Procedure A. MS (ESI$^+$) m/z: 395.2 [M+H]$^+$.

Compound 26 was then obtained by hydrolysis of the ester derivative (16 mg, 0.041 mmol) as described for compound 1, as a beige solid (12 mg, Y=77%). $^1$H NMR (400 MHz, ACETONE-d6) δ ppm 1.29-1.42 (m, 7H) 1.49-1.65 (m, 4H) 2.28 (t, J=7.31 Hz, 2H) 2.69 (t, J=7.63 Hz, 2H) 4.25 (q, J=7.31 Hz, 2H) 7.40-7.51 (m, 3H) 7.58-7.69 (m, 2H). MS (ESI$^+$) m/z: 381.2 [M+H]$^+$.

Example 27

Synthesis of 7-(3-(N-(2-methyl-2H-tetrazol-5-yl) sulfamoyl)phenyl)heptanoic Acid (27)

Starting from 2-methyl-2H-tetrazol-5-amine (15 mg, 0.15 mmol) methyl 7-(3-(N-(2-methyl-2H-tetrazol-5-yl)sulfamoyl)phenyl)heptanoate was obtained (10 mg, Y=17%) as described in Procedure A. MS (ESI$^+$) m/z: 382.2 [M+H]$^+$.

Compound 27 was then obtained by hydrolysis of the ester derivative (3.6 mg, 9.4 µmol) as described for compound 1, as a white solid (2.0 mg, Y=58%). $^1$H NMR (400

MHz, ACETONE-d6) δ ppm 1.33-1.44 (m, 4H) 1.49-1.69 (m, 4H) 2.28 (t, J=6.68 Hz, 2H) 2.81 (t, J=7.14 Hz, 2H) 3.58 (s, 3H) 7.03 (s, 1H) 7.48-7.53 (m, 2H) 7.77-7.96 (m, 1H). MS (ESI$^+$) m/z: 368.2 [M+H]$^+$.

Example 28

Synthesis of 7-(3-(N-(4-methyl-4,5-dihydrooxazol-2-yl)sulfamoyl)phenyl) heptanoic Acid (28)

Starting from 4-methyl-4,5-dihydrooxazol-2-amine (15 mg, 0.15 mmol) methyl 7-(3-(N-(4-methyl-4,5-dihydrooxazol-2-yl)sulfamoyl)heptanoate was obtained (9.5 mg, Y=16%) as described in Procedure A. MS (ESI$^+$) m/z: 383.2 [M+H]$^+$.

Compound 28 was then obtained by hydrolysis of the ester derivative (3.6 mg, 9.4 μmol) as described for compound 1, as a white solid (3.0 mg, Y=87%). $^1$H NMR (400 MHz, ACETONE-d6) δ ppm 1.23-1.43 (m, 5H) 1.53-1.69 (m, 4H) 2.28 (t, J=7.30 Hz, 2H) 2.70 (t, J=9.50 Hz, 2H) 3.98-4.12 (m, 1H) 4.24-4.37 (m, 1H) 4.57-4.66 (m, 1H) 7.43 (m, 1H) 7.56-7.77 (m, 2H) 8.18 (br s, 1H). MS (ESI$^+$) m/z: 369.2 [M+H]$^+$.

Example 29

Synthesis of 7-(3-(N-(3a,4,5,6,7,7a-hexahydro-1H-benzo[d]imidazol-2-yl)sulfamoyl)phenyl)heptanoic Acid (29)

Starting from 3a,4,5,6,7,7a-hexahydro-1H-benzo[d]imidazol-2-amine (18 mg, 0.13 mmol) 2-ethylhexyl 7-(3-(N-(3a,4,5,6,7,7a-hexahydro-1H-benzo[d]imidazol-2-yl)sulfamoyl)phenyl)heptanoate was obtained (31 mg, Y=45%) as described in Procedure A. MS (ESI$^+$) m/z: 520.4 [M+H]$^+$.

Compound 29 was then obtained by hydrolysis of the ester derivative (4.0 mg, 7.7 μmol) as described for compound 1, as a white solid (3.0 mg, Y=96%). $^1$H NMR (400 MHz, Solvent) δ ppm 1.56-1.71 (m, 4H) 1.74-1.84 (m, 6H) 2.01-2.16 (m, 6H) 2.26 (t, J=7.02 Hz, 2H) 2.70 (t, J=6.82 Hz, 2H) 3.16 (br d, J=8.27 Hz, 1H) 3.57-3.64 (m, 1H) 7.02-7.06 (m, 1H) 7.12 (br s, 1H) 7.38-7.41 (m, 1H) 7.63-7.72 (m, 2H). MS (ESI$^+$) m/z: 408.2 [M+H]$^+$.

Example 30

Synthesis of 7-(3-(N-(3-phenylisothiazol-4-yl)sulfamoyl)phenyl)heptanoic Acid (30)

Starting from 3-phenylisothiazol-4-amine (23 mg, 0.13 mmol) 2-ethylhexyl 7-(3-(N-(3-phenylisothiazol-4-yl)sulfamoyl)phenyl)heptanoate was obtained (23 mg, Y=31%) as described in Procedure A. MS (ESI$^+$) m/z: 557.3 [M+H]$^+$.

Compound 30 was then obtained by hydrolysis of the ester derivative (3.0 mg, 5.4 μmol) as described for compound 1, as a yellow solid (2.0 mg, Y=84%). $^1$H NMR (300 MHz, CHLOROFORM-d) δ ppm 1.16-1.43 (m, 4H) 1.55-1.71 (m, 4H) 2.22 (t, J=7.00 Hz, 2H) 2.46 (t, J=6.69 Hz, 2H) 7.00 (s, 1H) 7.39-7.70 (m, 6H) 7.84-7.98 (m, 4H). MS (ESI$^+$) m/z: 445.2 [M+H]$^+$.

Example 31

Synthesis of 7-(3-(N-(4-hydroxy-2,6-dimethylphenyl)sulfamoyl)phenyl) heptanoic Acid (31)

Compound 8 (11 mg, 0,026 mmol) was dissolved in dry DCM (0.5 ml). The mixture was cooled to 0° C. and Boron tribromide 1M in DCM (0.072 mL, 0,072 mmol) was added. The mixture was allowed to warm to RT, and stirred for 5 hours. Water (1 mL) was added and the mixture was stirred for 10 minutes. The organic layer was concentrated under reduced pressure and the residue was purified over silica (DCM/MeOH 95/5) to afford 31 as a yellow liquid (2.6 mg, Y=24%). $^1$H NMR (300 MHz, CHLOROFORM-d) δ ppm 1.16-1.70 (m, 8H) 1.85 (s, 6H) 2.38 (t, J=7.03 Hz, 2H) 2.57 (t, J=7.46 Hz, 2H) 6.03 (br s, 1H) 6.48 (s, 2H) 7.30-7.46 (m, 3H) 7.52-7.76 (m, 1H). MS (ESI$^+$) m/z: 406.2 [M+H]$^+$.

Example 32

Synthesis of 7-(3-(N-(3,5-dimethyl-[1,1'-biphenyl]-4-yl)sulfamoyl)phenyl) heptanoic Acid (32)

Starting from 4-bromo-2,6-dimethylaniline (1.0 g, 5.0 mmol), 3,5-dimethyl-[1,1'-biphenyl]-4-amine (354 mg, Y=36%) was synthesized by Suzuki coupling as described for compound 9. MS (ESI$^+$) m/z: 198.2 [M+H]$^+$.

Starting from 3,5-dimethyl-[1,1'-biphenyl]-4-amine (30.9 mg, 0.157 mmol) methyl 7-(3-(N-(3,5-dimethyl-[1,1'-biphenyl]-4-yl)sulfamoyl)phenyl)heptanoate was obtained (13 mg, Y=17%) as described in Procedure A. MS (ESI$^+$) m/z 480.2 [M+H]$^+$.

Compound 32 was then obtained by hydrolysis of the ester derivative (13 mg, 0.027 mmol) as described for compound 1, as a brown oil (11 mg, Y=87%). $^1$H NMR (300 MHz, CHLOROFORM-d) δ ppm 1.22-1.36 (m, 4H) 1.49-1.69 (m, 4H) 2.08 (s, 6H) 2.29 (t, J=7.30 Hz, 2H) 2.60 (t, J=7.30 Hz, 2H) 6.32 (br s, 1H) 7.22-7.27 (m, 2H) 7.31-7.46 (m, 5H) 7.48-7.62 (m, 4H). MS (ESI$^+$) m/z 488.3 [M+Na]$^+$.

Example 33

Synthesis of 7-(3-(N-(2,6-dimethyl-4-phenoxyphenyl)sulfamoyl)phenyl) heptanoic Acid (33)

4-Bromo-2,6-dimethylaniline (500 mg, 2.50 mmol), phenol (282 mg, 3.00 mmol), copper(I) iodide (47.6 mg, 0.250 mmol), 1-butyl-1H-imidazole (0.164 mL, 1.25 mmol) and potassium carbonate (691 mg, 5.00 mmol) were suspended in Toluene Dry (2.5 ml). The mixture was irradiated with microwaves for 2 h at 150° C. After removing the solvent under reduced pressure, the residue was taken with AcOEt (15 mL) and washed with brine (2×10 mL). The organic layer was concentrated under reduced pressure and the residue was purified by semi-preparative HPLC-UV, to afford 2,6-dimethyl-4-phenoxyaniline as a brown solid (280 mg, Y=52%). MS (ESI$^+$) m/z 214.1 [M+H]$^+$.

Starting from 2,6-dimethyl-4-phenoxyaniline (33.4 mg, 0.157 mmol) methyl 7-(3-(N-(2,6-dimethyl-4-phenoxyphenyl)sulfamoyl)phenyl)heptanoate was obtained (17 mg, Y=22%) as described in Procedure A. MS (ESI$^+$) m/z: 518.2 [M+Na]$^+$.

Compound 33 was then obtained by hydrolysis of the ester derivative (17 mg, 0.034 mmol) as described for compound 1, as a brown oil (16 mg, Y=97%). $^1$H NMR (300 MHz, CHLOROFORM-d) δ ppm 1.23-1.37 (m, 4H) 1.52-1.68 (m, 4H) 1.97 (s, 6H) 2.33 (t, J=7.30 Hz, 2H) 2.63 (t, J=7.30 Hz, 2H) 6.21 (br s, 1H) 6.63 (s, 2H) 6.99 (d, J=8.12 Hz, 2H) 7.05-7.19 (m, 1H) 7.29-7.43 (m, 4H) 7.45-7.60 (m, 2H). MS (ESI$^+$) m/z: 504.2 [M+Na]$^+$.

Example 34

Synthesis of 7-(3-(N-(4-(benzyloxy)-2,6-dimethylphenyl)sulfamoyl)phenyl) heptanoic Acid (34)

4-amino-3,5-dimethylphenol (400 mg, 2.92 mmol) and di-tert-butyl-dicarbonate were dissolved in acetone (3 mL) and the mixture was stirred for 22 hours. The solvent was removed under reduced pressure and hexane (10 mL) was added to the residue. The mixture was stirred for 70 hours, then filtered. The solid residue was purified on silica (Hex/AcOEt 9/1) to afford tert-butyl (4-hydroxy-2,6-dimethylphenyl)carbamate as a white solid (433 mg, Y=63%). MS (ESI$^+$) m/z: 260.1 [M+Na]$^+$.

Tert-butyl (4-hydroxy-2,6-dimethylphenyl)carbamate (380 mg, 1.60 mmol) was dissolved in N,N-Dimethylformamide Dry (10 mL). (Bromomethyl)benzene (0.381 ml, 3.20 mmol), potassium carbonate (885 mg, 6.41 mmol) and potassium iodide (798 mg, 4.80 mmol) were added, and the mixture was irradiated with microwaves for 2 h at 100° C. AcOEt (20 mL) was added, and the mixture was washed with brine (2×10 mL). The organic layer was concentrated under reduced pressure and the residue was purified by semi-preparative HPLC-UV, to afford tert-butyl (4-(benzyloxy)-2,6-dimethylphenyl)carbamate (353 mg, Y=67%). MS (ESI$^+$) m/z: 350.2 [M+Na]$^+$.

Tert-butyl (4-(benzyloxy)-2,6-dimethylphenyl)carbamate (353 mg, 1.08 mmol) was dissolved in Dichloromethane Dry (2 mL). Hydrogen chloride 4M in dioxane (0.54 mL, 2.16 mmol) was added and the mixture was stirred for 12 hours. The solvent was removed under reduced pressure to afford 4-(benzyloxy)-2,6-dimethylaniline, hydrochloride salt (285 mg, Y=quant.) as a beige solid. MS (ESI$^+$) m/z: 228.2 [M+H]$^+$.

Starting from 4-(benzyloxy)-2,6-dimethylaniline, hydrochloride salt (41.4 mg, 0.157 mmol) methyl 7-(3-(N-(4-(benzyloxy)-2,6-dimethylphenyl)sulfamoyl)phenyl) heptanoate was obtained (27 mg, Y=34%) as described in Procedure A. MS (ESI$^+$) m/z: 532.3 [M+Na]$^+$.

Compound 34 was then obtained by hydrolysis of the ester derivative (27 mg, 0.053 mmol) as described for compound 1, as a beige solid (23 mg, Y=87%). $^1$H NMR (300 MHz, CHLOROFORM-d) δ ppm 1.24-1.38 (m, 4H) 1.50-1.70 (m, 4H) 1.97 (s, 6H) 2.33 (t, J=7.30 Hz, 2H) 2.61 (t, J=7.58 Hz, 2H) 5.00 (s, 2H) 6.19 (br s, 1H) 6.62 (s, 2H) 7.31-7.45 (m, 7H) 7.50-7.58 (m, 2H). MS (ESI$^+$) m/z: 496.2 [M+H]$^+$.

Example 35

Synthesis of 7-(3-(N-(2,6-dimethyl-4-(3-(methylsulfonyl)propoxy)phenyl) sulfamoyl)phenyl)heptanoic Acid (35)

4-Methylbenzene-1-sulfonyl chloride (759 mg, 3.98 mmol), 3-(methylsulfonyl)propan-1-ol (500 mg, 3.62 mmol) and triethyl amine (0.555 mL, 3.98 mmol) were dissolved in Dichloromethane Dry (5 mL) under nitrogen atmosphere, and the mixture was stirred for 12 hours. The solvent was removed under reduced pressure and the residue was purified by semi-preparative HPLC-UV, to afford 3-(methylsulfonyl)propyl 4-methylbenzenesulfonate (881 mg, Y=83%) as a white solid. MS (ESI$^+$) m/z: 293.1 [M+H]$^+$.

Tert-butyl (4-hydroxy-2,6-dimethylphenyl)carbamate (which was synthesized as reported in the synthesis of compound 34) (269 mg, 1.13 mmol), 3-(methylsulfonyl)propyl 4-methylbenzenesulfonate (398 mg, 1.36 mmol) and potassium carbonate (188 mg, 1.36 mmol) were dissolved in N,N-Dimethylformamide Dry (2.5 ml) and the mixture was stirred at 80° C. under nitrogen atmosphere for 12 hours. AcOEt (20 mL) was added, and the mixture was washed with brine (2×10 mL). The organic layer was concentrated under reduced pressure and the residue was purified by semi-preparative HPLC-UV, to afford tert-butyl (2,6-dimethyl-4-(3-(methylsulfonyl)propoxy)phenyl)carbamate (375 mg, Y=93%) as a white solid. MS (ESI$^+$) m/z: 380.2 [M+Na]$^+$.

Starting from tert-butyl (2,6-dimethyl-4-(3-(methylsulfonyl)propoxy)phenyl)carbamate (375 mg, 1.05 mmol), 2,6-dimethyl-4-(3-(methylsulfonyl)propoxy)aniline, hydrochloride salt (309 mg, Y=quant.) was obtained as reported in the synthesis of compound 34. MS (ESI$^+$) m/z: 258.1 [M+H]$^+$.

Starting from 2,6-dimethyl-4-(3-(methylsulfonyl)propoxy)aniline, hydrochloride salt (46.1 mg, 0.157 mmol) methyl 7-(3-(N-(2,6-dimethyl-4-(3-(methylsulfonyl)propoxy)phenyl)sulfamoyl) phenyl)heptanoate was obtained (33 mg, Y=39%) as described in Procedure A. MS (ESI$^+$) m/z: 562.3 [M+Na]$^+$.

Compound 35 was then obtained by hydrolysis of the ester derivative (20 mg, 0.046 mmol) as described for compound 1, as a white solid (23 mg, Y=83%). $^1$H NMR (300 MHz, CHLOROFORM-d) δ ppm 1.24-1.43 (m, 4H) 1.51-1.67 (m, 4H) 1.96 (s, 6H) 2.26-2.41 (m, 4H) 2.61 (t, J=7.58 Hz, 2H) 2.97 (s, 3H) 3.22-3.31 (m, 2H) 4.04 (t, J=5.68 Hz, 2H) 6.32 (br s, 1H) 6.52 (s, 2H) 7.33-7.41 (m, 2H) 7.48-7.58 (m, 2H) 9.36 (br s, 2H). MS (ESI$^+$) m/z: 526.2 [M+H]$^+$.

Example 36

GPR120/40 Activation: In Vitro $Ca^{2+}$ Mobilization

The activation of GPR120/40 by all compounds was determined by measuring changes in intracellular calcium levels using a $Ca^{2+}$ sensitive fluorescent dye.

The experiments were performed using CHO-k1 cells stably expressing the human GPR120 or GPR40. Cells were seeded 10000 cells/well in 384-plates in complete medium and grown overnight at 37° C., 5% CO2. 24 h after seeding, cell culture media was removed and cells were loaded with the fluorescent $Ca^{2+}$ indicator (Fluo-8 NW dye in Tyrode's buffer). Dye-loaded cell plates were incubated for 1 h at room temperature under a yellow light sodium lamp.

Cell were treated with test compounds and controls at 10, 30 and 60 μM. The kinetic response was monitored over a period of 7 minutes (using FLIPRTETRA system). A second injection of 3× concentrated reference agonist at ~EC50 were then administered to cells and the signal of the emitted fluorescence was measured over a period of additional 3 minutes. The agonist effect is expressed as a percentage of activation, with 100% activation being a result in which the Response Values of the test wells reach a level identical to the one of the Stimulator Controls (alpha linolenic acid reference agonist EC100). 0% activation is a result in which the Response Values of the test wells reach a level identical to the one of the Neutral Controls (assay buffer) in the AGO_KRV (Agonist Kinetic Response Value) response value. Results obtained with each compound were reported in Table 1.

Example 37

GPR120/40 Activation: In Vitro GLP-1 Secretion $2\times10^5$ STC-1 cells were seeded in a 12-plate and 24 hours later were treated with selected compounds. $1\times10^6$ NCI-H716 cells were differentiated in matrigel-coated 12-plate and treated 48 h hours later.

The day of the experiment, wells were washed once with 1 ml of PBS and then cells were stimulated with 0.5 ml of DMEM (w/o serum, w/o phenol-red) containing 30 μM of selected compounds in STC1 and 100 μM in differentiated NCIH716 for 30 minutes. DMSO has been used as negative control, α-linolenic acid (ALA) (endogenous agonist) as positive control. After stimulations, supernatants were collected, centrifuged at 4000 rpm for 4' at 4° C., and used for the GLP1 detection by ELISA.

Aryl-sulfonamide compounds were tested in STC1 cells and the results were shown in Table 1.

The most active compounds, 1, 2, 3, 4, 6, 7, 9, 10, 11, and 33, showed a significant agonistic activity on GPR120 and GPR40 (measured as $AC_{50}$ value in the calcium mobilization assay) in the low microMolar range. The same compounds were also found efficacious in GLP-1 secretion both in STC1 (murine) and NCI-H716 (human) entero endocrine cells, thus confirm the potential of the compounds for further characterization.

TABLE 1

| Ex. | Structure | Chemical Name | $Ca^{2+}$ hGPR120 | $Ca^{2+}$ hGPR40 | GLP-1 RELEASE STC-1* | GLP-1 RELEASE NCI** |
|---|---|---|---|---|---|---|
| 1 | 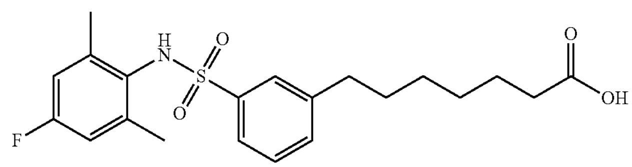 [SMILES: Cc1cc(F)cc(C)c1NS(=O)(=O)c1cccc(CCCCCCC(=O)O)c1] | 7-(3-(N-(4-fluoro-2,6-dimethylphenyl)sulfamoyl)phenyl)heptanoic acid | AC50 = 5.24 μM | AC50 = 140 μM | 1.87 ± 0.5 | 1.08 ± 0.10 |
| 2 | 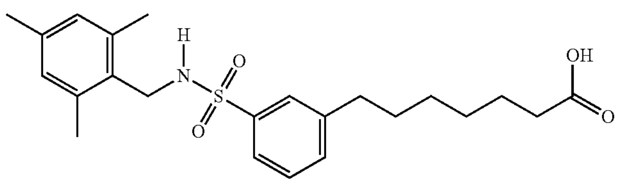 [SMILES: Cc1cc(C)c(CNS(=O)(=O)c2cccc(CCCCCCC(=O)O)c2)c(C)c1] | 7-(3-(N-(2,4,6-trimethylbenzyl)sulfamoyl)phenyl)heptanoic acid | AC50 = 7.09 μM | AC50 = 11.2 μM | 3.2 ± 0.47 | 2.1 ± 0.52 |
| 3 | 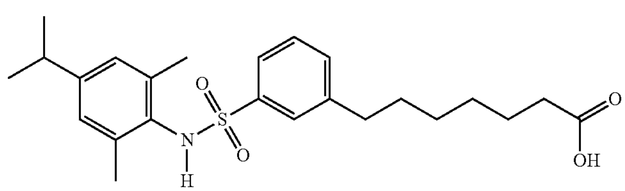 [SMILES: Cc1cc(C(C)C)cc(C)c1NS(=O)(=O)c1cccc(CCCCCCC(=O)O)c1] | 7-(3-(N-(4-isopropyl-2,6-dimethylphenyl)sulfamoyl)phenyl)heptanoic acid | AC50 = 1.98 μM | AC50 = 12.9 μM | 2.7 ± 0.31 | 2.5 ± 0.11 |
| 4 | 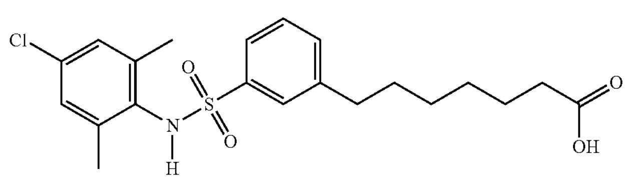 [SMILES: Cc1cc(Cl)cc(C)c1NS(=O)(=O)c1cccc(CCCCCCC(=O)O)c1] | 7-(3-(N-(4-chloro-2,6-dimethylphenyl)sulfamoyl)phenyl)heptanoic acid | AC50 = 4.36 μM | AC50 = 41.3 μM | 4.1 ± 0.54 | 1.92 ± 0.57 |
| 5 | 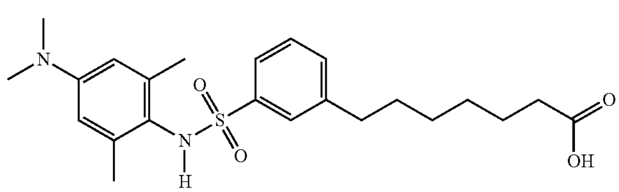 [SMILES: Cc1cc(N(C)C)cc(C)c1NS(=O)(=O)c1cccc(CCCCCCC(=O)O)c1] | 7-(3-(N-(4-(dimethylamino)-2,6-dimethylphenyl)sulfamoyl)phenyl)heptanoic acid | AC50 = 7.9 μM | AC50 = 10.4 μM | 4.0 ± 0.27 | 1.92 ± 0.14 |
| 6 | 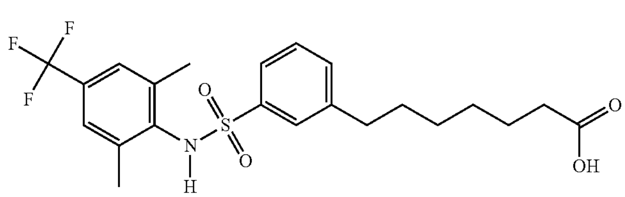 [SMILES: Cc1cc(C(F)(F)F)cc(C)c1NS(=O)(=O)c1cccc(CCCCCCC(=O)O)c1] | 7-(3-(N-(2,6-dimethyl-4-(trifluoromethyl)phenyl)sulfamoyl)phenyl)heptanoic acid | AC50 = 6 μM | AC50 = 11.7 μM | 4.2 ± 0.45 | 2.54 ± 0.52 |

TABLE 1-continued

| Ex. | Structure | Chemical Name | Ca²⁺ hGPR120 | Ca²⁺ hGPR40 | GLP-1 RELEASE STC-1* | GLP-1 RELEASE NCI** |
|---|---|---|---|---|---|---|
| 7 | 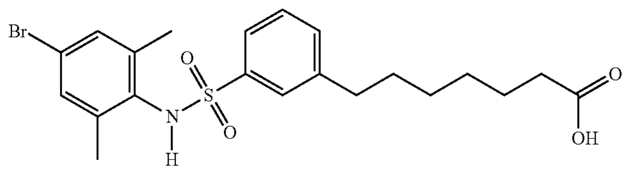 | 7-(3-(N-(4-bromo-2,6-dimethylphenyl)sulfamoyl)phenyl)heptanoic acid | AC50 = 5.72 μM | AC50 = 19.8 μM | 1.8 ± 0.24 | 1.9 ± 0.15 |
| 8 | 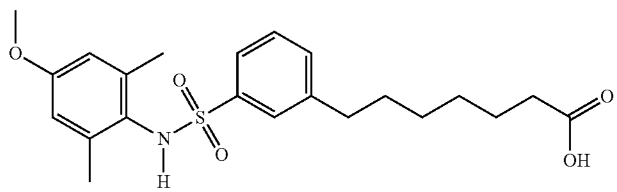 [SMILES: COc1cc(C)c(NS(=O)(=O)c2cccc(CCCCCCC(=O)O)c2)c(C)c1] | 7-(3-(N-(4-methoxy-2,6-dimethylphenyl)sulfamoyl)phenyl)heptanoic acid | AC50 = 11.7 μM | AC50 = 4.7 μM | 1.7 ± 0.12 | 2.1 ± 0.08 |
| 9 | 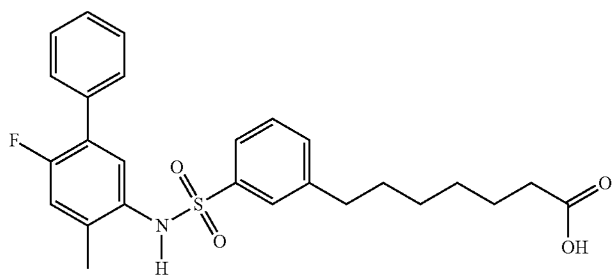 [SMILES: Cc1cc(F)c(-c2ccccc2)cc1NS(=O)(=O)c1cccc(CCCCCCC(=O)O)c1] | 7-(3-(N-(6-fluoro-4-methyl-[1,1'-biphenyl]-3-yl)sulfamoyl)phenyl)heptanoic acid | AC50 = 11.2 μM | AC50 = 8.9 μM | 14.5 ± 1.24 | 6.23 ± 1.12 |
| 10 | 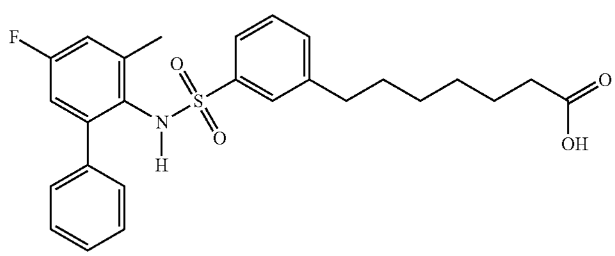 [SMILES: Cc1cc(F)cc(-c2ccccc2)c1NS(=O)(=O)c1cccc(CCCCCCC(=O)O)c1] | 7-(3-(N-(5-fluoro-3-methyl-[1,1'-biphenyl]-2-yl)sulfamoyl)phenyl)heptanoic acid | AC50 = 16.5 μM | AC50 = 12.8 μM | 4.74 ± 1.54 | 2.46 ± 0.48 |
| 11 | 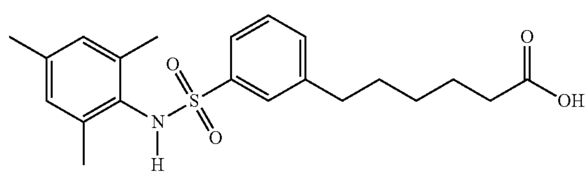 [SMILES: Cc1cc(C)c(NS(=O)(=O)c2cccc(CCCCCC(=O)O)c2)c(C)c1] | 6-{3-[(2,4,6-trimethylphenyl)sulfamoyl]phenyl}hexanoic acid | AC50 = 6.2 μM | Inactive | 1.71 ± 0.21 | 1.87 ± 0.27 |
| 12 | 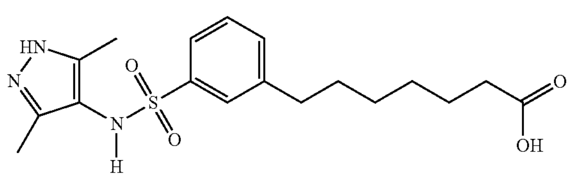 [SMILES: Cc1n[nH]c(C)c1NS(=O)(=O)c1cccc(CCCCCCC(=O)O)c1] | 7-(3-(N-(3,5-dimethyl-1H-pyrazol-4-yl)sulfamoyl)phenyl)heptanoic acid | AC50 = 13.1 μM | AC50 = 10.7 μM | 1.04 ± 0.32 | 1.41 ± 0.36 |
| 13 | 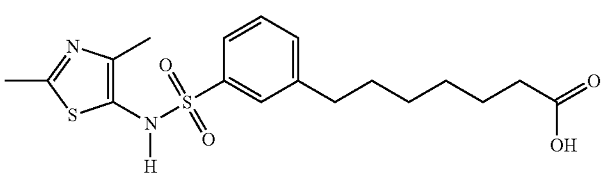 [SMILES: Cc1nc(C)c(NS(=O)(=O)c2cccc(CCCCCCC(=O)O)c2)s1] | 7-(3-(N-(2,4-dimethylthiazol-5-yl)sulfamoyl)phenyl)heptanoic acid | AC50 = 15.2 μM | AC50 = 23.9 μM | 1.13 ± 0.15 | 1.03 ± 0.17 |

TABLE 1-continued

| Ex. | Structure | Chemical Name | Ca²⁺ hGPR120 | Ca²⁺ hGPR40 | GLP-1 RELEASE STC-1* | GLP-1 RELEASE NCI** |
|---|---|---|---|---|---|---|
| 14 | 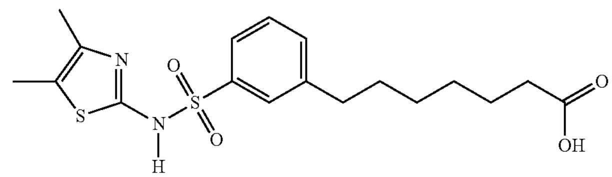 [SMILES: Cc1nc(NS(=O)(=O)c2cccc(CCCCCCC(=O)O)c2)sc1C] | 7-(3-(N-(4,5-dimethylthiazol-2-yl)sulfamoyl)phenyl)heptanoic acid | AC50 = 17.4 μM | AC50 = 20.8 μM | 1.37 ± 0.11 | 1.81 ± 0.67 |
| 15 | 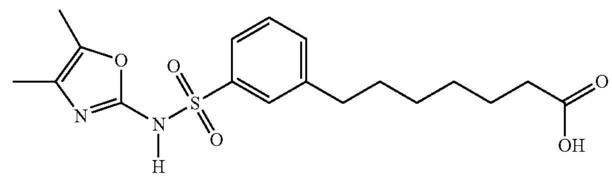 [SMILES: Cc1nc(NS(=O)(=O)c2cccc(CCCCCCC(=O)O)c2)oc1C] | 7-(3-(N-(4,5-dimethyloxazol-2-yl)sulfamoyl)phenyl)heptanoic acid | AC50 = 24.1 μM | AC50 = 27.5 μM | 1.19 ± 0.89 | 1.80 ± 0.91 |
| 16 | 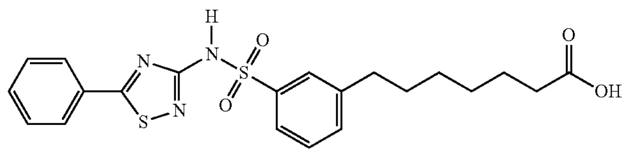 [SMILES: O=C(O)CCCCCCc1cccc(S(=O)(=O)Nc2nsc(-c3ccccc3)n2)c1] | 7-(3-(N-(5-phenyl-1,2,4-thiadiazol-3-yl)sulfamoyl)phenyl)heptanoic acid | AC50 = 25.9 μM | AC50 = 17.2 μM | 1.31 ± 0.32 | 1.69 ± 0.14 |
| 17 | 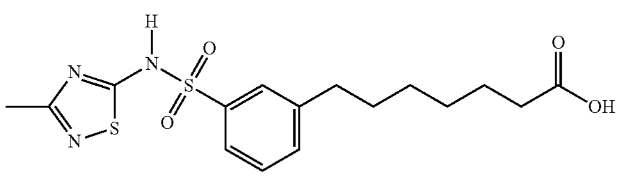 [SMILES: Cc1nsc(NS(=O)(=O)c2cccc(CCCCCCC(=O)O)c2)n1] | 7-(3-(N-(3-methyl-1,2,4-thiadiazol-5-yl)sulfamoyl)phenyl)heptanoic acid | AC50 = 22.3 μM | AC50 = 13.9 μM | 1.90 ± 0.51 | 2.19 ± 1.22 |
| 18 | 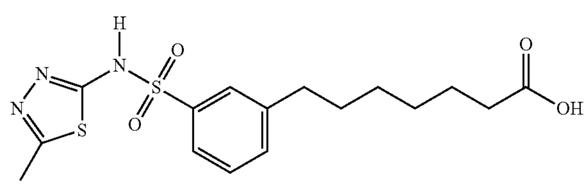 [SMILES: Cc1nnc(NS(=O)(=O)c2cccc(CCCCCCC(=O)O)c2)s1] | 7-(3-(N-(5-methyl-1,3,4-thiadiazol-2-yl)sulfamoyl)phenyl)heptanoic acid | AC50 = 27.8 μM | AC50 = 22.4 μM | 1.98 ± 0.37 | 1.25 ± 0.80 |
| 19 | 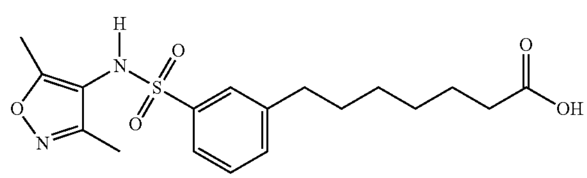 [SMILES: Cc1noc(C)c1NS(=O)(=O)c1cccc(CCCCCCC(=O)O)c1] | 7-(3-(N-(3,5-dimethylisoxazol-4-yl)sulfamoyl)phenyl)heptanoic acid | AC50 = 17.6 μM | AC50 = 12.1 μM | 2.57 ± 0.56 | 2.24 ± 0.39 |
| 20 | 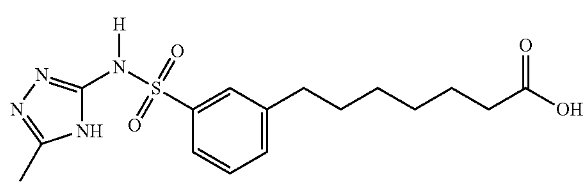 [SMILES: Cc1nnc(NS(=O)(=O)c2cccc(CCCCCCC(=O)O)c2)[nH]1] | 7-(3-(N-(5-methyl-4H-1,2,4-triazol-3-yl)sulfamoyl)phenyl)heptanoic acid | AC50 = 6.5 μM | AC50 = 8.2 μM | 3.36 ± 0.37 | 3.31 ± 0.28 |
| 21 | 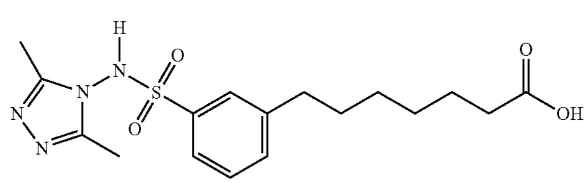 [SMILES: Cc1nnc(C)n1NS(=O)(=O)c1cccc(CCCCCCC(=O)O)c1] | 7-(3-(N-(3,5-dimethyl-4H-1,2,4-triazol-4-yl)sulfamoyl)phenyl)heptanoic acid | AC50 = 17.0 μM | AC50 = 7.9 μM | 2.23 ± 0.98 | 2.57 ± 0.91 |

TABLE 1-continued

| Ex. | Structure | Chemical Name | Ca²⁺ hGPR120 | Ca²⁺ hGPR40 | GLP-1 RELEASE STC-1* | GLP-1 RELEASE NCI** |
|---|---|---|---|---|---|---|
| 22 | 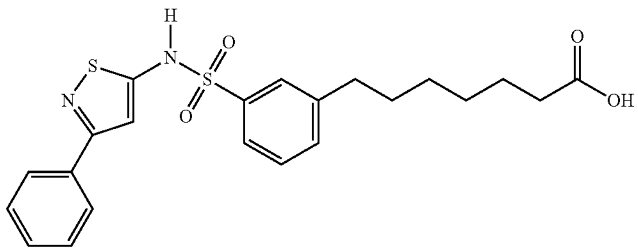 [SMILES: O=C(O)CCCCCCc1cccc(S(=O)(=O)Nc2cc(-c3ccccc3)ns2)c1] | 7-(3-(N-(3-phenylisothiazol-5-yl)sulfamoyl)phenyl)heptanoic acid | AC50 = 10.2 μM | AC50 = 11.7 μM | 3.13 ± 1.26 | 3.71 ± 0.67 |
| 23 | 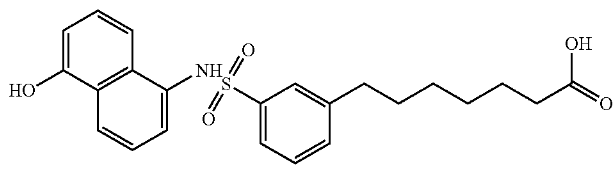 | 7-{3-[(5-hydroxy-naphthalen-1-yl)sulfamoyl]phenyl}heptanoic acid | AC50 = 7.1 μM | AC50 = 8.2 μM | 4.34 ± 0.51 | 4.69 ± 0.41 |
| 24 | 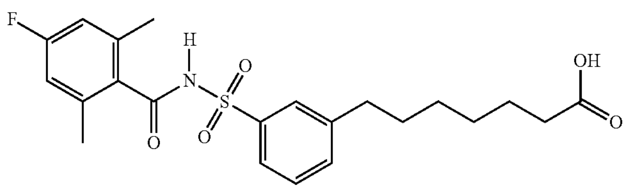 [SMILES: Cc1cc(F)cc(C)c1C(=O)NS(=O)(=O)c1cccc(CCCCCCC(=O)O)c1] | 7-{3-[(4-fluoro-2,6-dimethyl-benzoyl)sulfamoyl]phenyl}heptanoic acid | AC50 = 5.9 μM | AC50 = 13.3 μM | 4.19 ± 0.72 | 5.01 ± 0.99 |
| 25 | 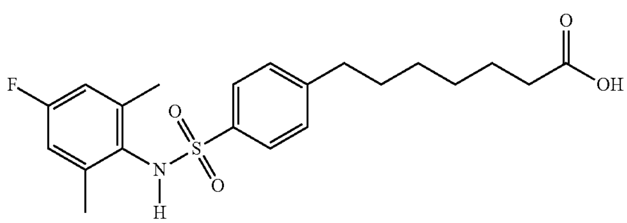 [SMILES: Cc1cc(F)cc(C)c1NS(=O)(=O)c1ccc(CCCCCCC(=O)O)cc1] | 7-{4-[(4-fluoro-2,6-dimethyl-phenyl)sulfamoyl]phenyl}heptanoic acid | AC50 = 4.3 μM | AC50 = 6.1 μM | 4.1 ± 0.78 | 3.2 ± 0.31 |
| 26 | 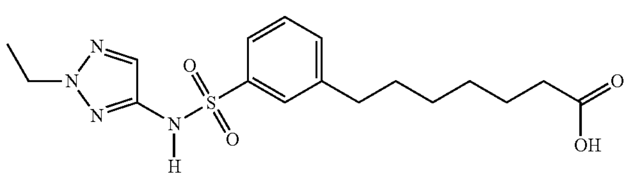 [SMILES: CCn1ncc(NS(=O)(=O)c2cccc(CCCCCCC(=O)O)c2)n1] | 7-(3-(N-(2-ethyl-2H-1,2,3-triazol-4-yl)sulfamoyl)phenyl)heptanoic acid | AC50 = 18.9 μM | AC50 = 20.1 μM | 1.82 ± 0.41 | 2.81 ± 0.72 |
| 27 | 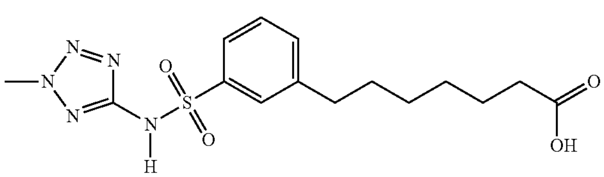 [SMILES: Cn1nnc(NS(=O)(=O)c2cccc(CCCCCCC(=O)O)c2)n1] | 7-(3-(N-(2-methyl-2H-tetrazol-5-yl)sulfamoyl)phenyl)heptanoic acid | AC50 = 10.1 μM | AC50 = 10.7 μM | 1.99 ± 0.51 | 2.89 ± 0.55 |
| 28 | 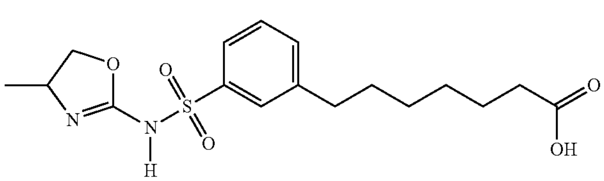 [SMILES: CC1COC(NS(=O)(=O)c2cccc(CCCCCCC(=O)O)c2)=N1] | 7-(3-(N-(4-methyl-4,5-dihydro-oxazol-2-yl)sulfamoyl)phenyl)heptanoic acid | AC50 = 16.1 μM | AC50 = 7.1 μM | 3.64 ± 0.43 | 3.88 ± 1.96 |

TABLE 1-continued

| Ex. | Structure | Chemical Name | Ca²⁺ hGPR120 | Ca²⁺ hGPR40 | GLP-1 RELEASE STC-1* | GLP-1 RELEASE NCI** |
|---|---|---|---|---|---|---|
| 29 | 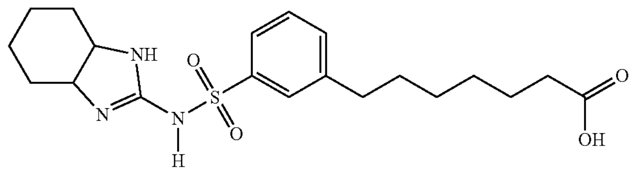 [SMILES: O=C(O)CCCCCCc1cccc(S(=O)(=O)NC2=NC3CCCCC3N2)c1] | 7-(3-(N-(3a,4,5,6,7,7a-hexahydro-1H-benzo[d]imidazol-2-yl)sulfamoyl)phenyl)heptanoic acid | AC50 = 12.4 μM | AC50 = 8.4 μM | 1.12 ± 0.40 | 2.89 ± 0.81 |
| 30 | 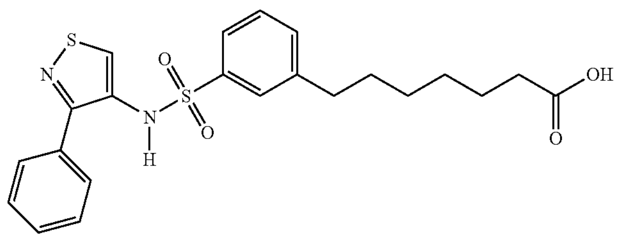 [SMILES: O=C(O)CCCCCCc1cccc(S(=O)(=O)Nc2csnc2-c2ccccc2)c1] | 7-(3-(N-(3-phenylisothiazol-4-yl)sulfamoyl)phenyl)heptanoic acid | AC50 = 37.1 μM | AC50 = 31.2 μM | 2.94 ± 1.12 | 2.13 ± 1.83 |
| 31 | 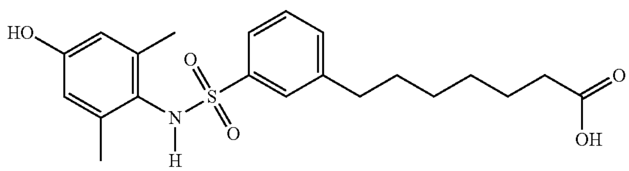 [SMILES: Cc1cc(O)cc(C)c1NS(=O)(=O)c1cccc(CCCCCCC(=O)O)c1] | 7-(3-(N-(4-hydroxy-2,6-dimethylphenyl)sulfamoyl)phenyl)heptanoic acid | AC50 = 9.3 μM | AC50 = 3.2 μM | 3.55 ± 0.87 | 3.70 ± 0.56 |
| 32 | 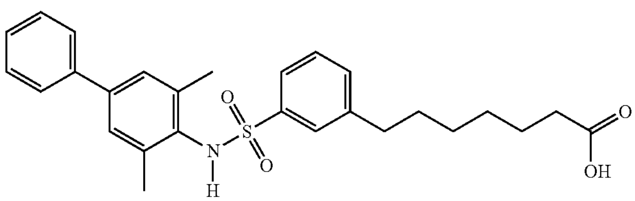 [SMILES: Cc1cc(-c2ccccc2)cc(C)c1NS(=O)(=O)c1cccc(CCCCCCC(=O)O)c1] | 7-(3-(N-(3,5-dimethyl-[1,1'-biphenyl]-4-yl)sulfamoyl)phenyl)heptanoic acid | AC50 = 11.1 μM | AC50 = 23.7 μM | 3.67 ± 0.90 | 4.51 ± 0.59 |
| 33 | 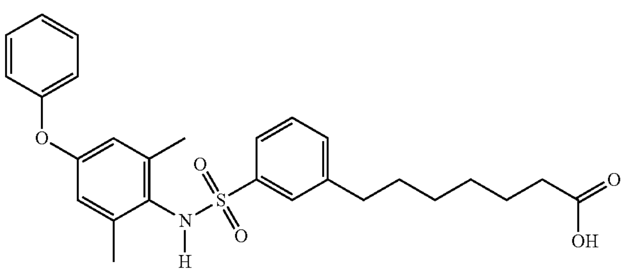 [SMILES: Cc1cc(Oc2ccccc2)cc(C)c1NS(=O)(=O)c1cccc(CCCCCCC(=O)O)c1] | 7-(3-(N-(2,6-dimethyl-4-phenoxyphenyl)sulfamoyl)phenyl)heptanoic acid | AC50 = 18 μM | Inactive | 3.0 ± 1.82 | 1.58 ± 1.27 |
| 34 | 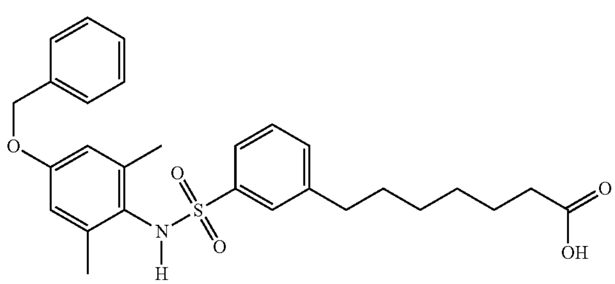 [SMILES: Cc1cc(OCc2ccccc2)cc(C)c1NS(=O)(=O)c1cccc(CCCCCCC(=O)O)c1] | 7-(3-(N-(4-(benzyloxy)-2,6-dimethylphenyl)sulfamoyl)phenyl)heptanoic acid | AC50 = 7.0 μM | AC50 = 12.4 μM | 5.5 ± 0.73 | 4.58 ± 0.26 |

TABLE 1-continued

| Ex. | Structure | Chemical Name | Ca²⁺ hGPR120 | Ca²⁺ hGPR40 | GLP-1 RELEASE STC-1* | GLP-1 RELEASE NCI** |
|---|---|---|---|---|---|---|
| 35 | 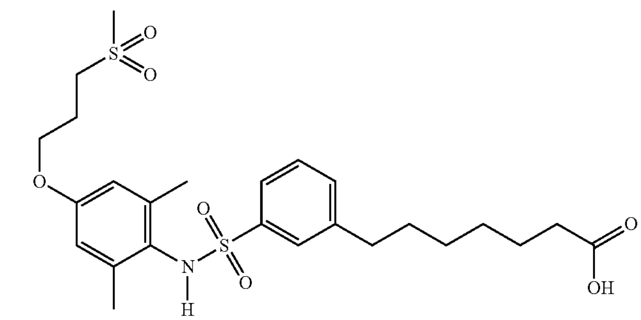 [SMILES: Cc1cc(OCCCS(C)(=O)=O)cc(C)c1NS(=O)(=O)c1cccc(CCCCCCC(=O)O)c1] | 7-(3-(N-(2,6-dimethyl-4-(3-(methylsulfonyl)propoxy)phenyl)sulfamoyl)phenyl)heptanoic acid | AC50 = 6.1 µM | AC50 = 2.3 µM | 4.3 ± 0.61 | 4.2 ± 0.25 |

*Fold of increase of the compound tested at 30 µM for 30 minutes over DMSO (ALA = 6.61 ± 2.45)
**Fold of increase of the compound tested at 100 µM for 30 minutes over DMSO (ALA = 1.52 ± 0.19)

The invention claimed is:

1. A compound of formula (I):

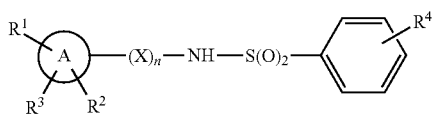

or a pharmaceutically acceptable salt thereof,
wherein:
A is a mono or di-carbocyclic residue, optionally partially or totally unsaturated, comprising carbon atoms and optionally one or more heteroatoms selected from N, S and O;
$R^1$, $R^2$, and $R^3$ are independently selected from the group consisting of —H, -halogen, —$CF_3$, —CN, —$CH_2CN$, —OMe, —$OCF_3$, —OH, phenyl, —OPh, —$OCH_2Ph$, —$OCH_2OMe$, —$OCH_2CN$—$NO_2$, —NR'R", linear or branched $C_1$-$C_6$ alkyl, —$O(CH_2)_p$—$S(O)_2Me$ and a five-membered ring heterocycle;
wherein R' and R" are independently —H or $C_1$-$C_4$ alkyl;
wherein phenyl and the five-membered ring heterocycle are independently unsubstituted or substituted with a group selected from the group consisting of linear or branched $C_1$-$C_4$ alkyl, halogen, —OMe and —OH;
p is 1 to 4;
X is —$CH_2$ or —C(O);
n is 0, 1 or 2;
$R^4$ is —Y—C(O)OH, wherein Y is a straight chain $C_4$-$C_{18}$ hydrocarbon, saturated or unsaturated; and
$R^4$ is in position meta or para on the aromatic ring;
wherein when A is phenyl, n is 0, and Y is a $C_4$ hydrocarbon, at least one of said $R^1$, $R^2$, $R^3$ is not hydrogen;
wherein when A is phenyl, n is 0, Y is a $C_4$ hydrocarbon, and $R^1$ and $R^2$ are hydrogen, $R^3$ is not Cl in position para on the aromatic ring.

2. The compound according to claim 1, wherein A is phenyl, naphthyl, biphenyl or a saturated or unsaturated five-membered ring heterocycle having 1, 2, 3 or 4 ring heteroatoms independently selected from N, O and S.

3. The compound according to claim 1, wherein the five-membered ring heterocycle is selected from the group consisting of thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, and benzimidazole, which rings may optionally be partially saturated.

4. The compound according to claim 1, wherein $R^1$, $R^2$, and $R^3$ are independently selected from the group consisting of —H, -halogen, —$CF_3$, —OMe, —OH, phenyl, —OPh, —$OCH_2Ph$, —$OCH_2OMe$, —$OCH_2CN$—$NO_2$, —$NH_2$, —$NMe_2$, linear or branched $C_1$-$C_6$ alkyl and —$O(CH_2)_p$—$S(O)_2Me$.

5. The compound according to claim 1, wherein n is 0 or 1.

6. The compound according to claim 1, wherein $R^4$ is in position meta on the aromatic ring.

7. The compound according to claim 1, wherein Y is a straight chain $C_6$-$C_{10}$ hydrocarbon which may be saturated or unsaturated.

8. The compound according to claim 1, which is selected from the group consisting of:
7-(3-(N-(4-fluoro-2,6-dimethylphenyl)sulfamoyl)phenyl)heptanoic acid;
7-(3-(N-(2,4,6-trimethylbenzyl)sulfamoyl)phenyl)heptanoic acid;
7-(3-(N-(4-isopropyl-2,6-dimethylphenyl)sulfamoyl)phenyl)heptanoic acid;
7-(3-(N-(4-chloro-2,6-dimethylphenyl)sulfamoyl)phenyl)heptanoic acid;
7-(3-(N-(4-(dimethylamino)-2,6-dimethylphenyl)sulfamoyl)phenyl)heptanoic acid;
7-(3-(N-(2,6-dimethyl-4-(trifluoromethyl)phenyl)sulfamoyl)phenyl)heptanoic acid;
7-(3-(N-(4-bromo-2,6-dimethylphenyl)sulfamoyl)phenyl)heptanoic acid;
7-(3-(N-(4-methoxy-2,6-dimethylphenyl)sulfamoyl)phenyl)heptanoic acid;
7-(3-(N-(6-fluoro-4-methyl-[1,1'-biphenyl]-3-yl)sulfamoyl)phenyl)heptanoic acid;
7-(3-(N-(5-fluoro-3-methyl-[1,1'-biphenyl]-2-yl)sulfamoyl)phenyl)heptanoic acid;
6-{3-[(2,4,6-trimethylphenyl)sulfamoyl]phenyl}hexanoic acid;
7-(3-(N-(3,5-dimethyl-1H-pyrazol-4-yl)sulfamoyl)phenyl)heptanoic acid;

7-(3-(N-(2,4-dimethylthiazol-5-yl)sulfamoyl)phenyl) heptanoic acid;
7-(3-(N-(4,5-dimethylthiazol-2-yl)sulfamoyl)phenyl) heptanoic acid;
7-(3-(N-(4,5-dimethyloxazol-2-yl)sulfamoyl)phenyl)heptanoic acid;
7-(3-(N-(5-phenyl-1,2,4-thiadiazol-3-yl)sulfamoyl)phenyl)heptanoic acid;
7-(3-(N-(3-methyl-1,2,4-thiadiazol-5-yl)sulfamoyl)phenyl)heptanoic acid;
7-(3-(N-(5-methyl-1,3,4-thiadiazol-2-yl)sulfamoyl)phenyl)heptanoic acid;
7-(3-(N-(3,5-dimethylisoxazol-4-yl)sulfamoyl)phenyl) heptanoic acid;
7-(3-(N-(5-methyl-4H-1,2,4-triazol-3-yl)sulfamoyl)phenyl)heptanoic acid;
7-(3-(N-(3,5-dimethyl-4H-1,2,4-triazol-4-yl)sulfamoyl) phenyl)heptanoic acid;
7-(3-(N-(3-phenylisothiazol-5-yl)sulfamoyl)phenyl)heptanoic acid;
7-{3-[(5-hydroxynaphthalen-1-yl)sulfamoyl] phenyl}heptanoic acid;
7-{3-[(4-fluoro-2,6-dimethylbenzoyl)sulfamoyl] phenyl}heptanoic acid;
7-{4-[(4-fluoro-2,6-dimethylphenyl)sulfamoyl] phenyl}heptanoic acid;
7-(3-(N-(2-ethyl-2H-1,2,3-triazol-4-yl)sulfamoyl)phenyl) heptanoic acid;
7-(3-(N-(2-methyl-2H-tetrazol-5-yl)sulfamoyl)phenyl) heptanoic acid;
7-(3-(N-(4-methyl-4,5-dihydrooxazol-2-yl)sulfamoyl) phenyl)heptanoic acid;
7-(3-(N-(3a,4,5,6,7,7a-hexahydro-1H-benzo[d]imidazol-2yl)sulfamoyl)phenyl) heptanoic acid;
7-(3-(N-(3-phenylisothiazol-4-yl)sulfamoyl)phenyl)heptanoic acid;
7-(3-(N-(4-hydroxy-2,6-dimethylphenyl)sulfamoyl)phenyl)heptanoic acid;
7-(3-(N-(3,5-dimethyl-[1,1'-biphenyl]-4-yl)sulfamoyl) phenyl)heptanoic acid;
7-(3-(N-(2,6-dimethyl-4-phenoxyphenyl)sulfamoyl)phenyl)heptanoic acid;
7-(3-(N-(4-(benzyloxy)-2,6-dimethylphenyl)sulfamoyl) phenyl)heptanoic acid; and
7-(3-(N-(2,6-dimethyl-4-(3(methylsulfonyl)propoxy) phenyl)sulfamoyl)phenyl)heptanoic acid.

9. The compound according to claim 8, which is selected from the group consisting of:
7-(3-(N-(4-fluoro-2,6-dimethylphenyl)sulfamoyl)phenyl) heptanoic acid;
7-(3-(N-(2,4,6-trimethylbenzyl)sulfamoyl)phenyl)heptanoic acid;
7-(3-(N-(4-isopropyl-2,6-dimethylphenyl)sulfamoyl)phenyl)heptanoic acid;
7-(3-(N-(4-chloro-2,6-dimethylphenyl)sulfamoyl)phenyl)heptanoic acid;
7-(3-(N-(2,6-dimethyl-4-(trifluoromethyl)phenyl)sulfamoyl)phenyl)heptanoic acid;
7-(3-(N-(4-bromo-2,6-dimethylphenyl)sulfamoyl)phenyl)heptanoic acid;
7-(3-(N-(6-fluoro-4-methyl-[1,1'-biphenyl]-3-yl)sulfamoyl)phenyl)heptanoic acid;
7-(3-(N-(5-fluoro-3-methyl-[1,1'-biphenyl]-2-yl)sulfamoyl)phenyl)heptanoic acid;
6-{3-[(2,4,6-trimethylphenyl)sulfamoyl] phenyl}hexanoic acid; and
7-(3-(N-(2,6-dimethyl-4-phenoxyphenyl)sulfamoyl)phenyl)heptanoic acid (33).

10. A method for the treatment of a disease or disorder modulated by GPR120 and/or GPR40 in a subject in need thereof, comprising administration of an effective amount of the compound according to claim 1, alone or in combination with one or more pharmaceutically acceptable excipients.

11. The method according to claim 10, wherein the disease or disorder is selected from the group consisting of diabetes, type 2 diabetes, impaired oral glucose tolerance, insulin resistance, obesity, obesity related disorders, metabolic syndrome, dyslipidemia, elevated LDL, elevated triglycerides, obesity induced inflammation, osteoporosis and obesity related cardiovascular disorders.

12. A pharmaceutical composition comprising as the active ingredient at least one compound according to claim 1, in combination with physiologically acceptable excipients.

13. The pharmaceutical composition according to claim 12, suitable to be administered by intravenous, intraperitoneal, inhalation, topical or oral route.

14. The pharmaceutical composition according to claim 12, in the form of a liquid or a solid.

15. The pharmaceutical composition according to claim 14, in the form of a capsule, tablet, coated tablet, syrup, powder, granules, cream, lotion, spray or ointment.

* * * * *

UNITED STATES PATENT AND TRADEMARK OFFICE
CERTIFICATE OF CORRECTION

PATENT NO. : 10,508,090 B2
APPLICATION NO. : 16/324243
DATED : December 17, 2019
INVENTOR(S) : Maria De Pizzol et al.

Page 1 of 1

It is certified that error appears in the above-identified patent and that said Letters Patent is hereby corrected as shown below:

On the Title Page

Under Applicant: The city should read Milano.

Under Inventors: The city of inventor one should read Milano.
      The city of inventor three should read Genova.
      The city of inventor seven should read Milano.

Under Assignee: The city should read Milano.

Signed and Sealed this
Twenty-fourth Day of March, 2020

Andrei Iancu
*Director of the United States Patent and Trademark Office*